(12) United States Patent
Adachi et al.

(10) Patent No.: US 8,849,391 B2
(45) Date of Patent: Sep. 30, 2014

(54) SPEECH SOUND INTELLIGIBILITY ASSESSMENT SYSTEM, AND METHOD AND PROGRAM THEREFOR

(75) Inventors: Shinobu Adachi, Nara (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 379 days.

(21) Appl. No.: 13/304,789

(22) Filed: Nov. 28, 2011

(65) Prior Publication Data

US 2012/0072213 A1 Mar. 22, 2012

Related U.S. Application Data

(63) Continuation of application No. PCT/JP2011/000006, filed on Jan. 5, 2011.

(30) Foreign Application Priority Data

Jan. 28, 2010 (JP) .................................. 2010-017207

(51) Int. Cl.
| | |
|---|---|
| *A61B 5/04* | (2006.01) |
| *A61B 5/12* | (2006.01) |
| *A61B 5/0484* | (2006.01) |
| *A61B 5/00* | (2006.01) |

(52) U.S. Cl.
CPC .................. *A61B 5/12* (2013.01); *A61B 5/7225* (2013.01); *A61B 5/04845* (2013.01)
USPC .......................................... 600/544; 600/559

(58) Field of Classification Search
USPC .................................................. 600/544, 559
See application file for complete search history.

(56) References Cited

U.S. PATENT DOCUMENTS

| 5,282,475 A | * | 2/1994 | Urbach et al. ................. 600/544 |
| 2006/0114222 A1 | * | 6/2006 | Araki et al. .................... 345/156 |
| 2008/0234596 A1 | * | 9/2008 | Park et al. ...................... 600/544 |
| 2010/0317988 A1 | * | 12/2010 | Terada et al. .................. 600/544 |

FOREIGN PATENT DOCUMENTS

| JP | 06-114038 A | 4/1994 |
| JP | 09-038069 A | 2/1997 |

OTHER PUBLICATIONS

International Search Report for corresponding International Application No. PCT/JP2011/000006 mailed Apr. 12, 2011.
Kazuoki Kodera, "Hochoki Fittingu No Kangaekata" (or "Concept of Hearing Aid Fitting"), Shindan to Chiryosha, 1999, p. 166-167 and concise explanation.

(Continued)

*Primary Examiner* — Simon Sing
(74) *Attorney, Agent, or Firm* — Renner, Otto, Boisselle & Sklar, LLP

(57) ABSTRACT

The speech sound intelligibility assessment system includes: an output section for presenting a speech sound to a user; a biological signal measurement section for measuring an electroencephalogram signal of the user; a positive component determination section for determining presence/absence of a positive component of an event-related potential in the electroencephalogram signal in a zone from 600 ms to 800 ms from a starting point, which is a point in time at which the output section presents a speech sound; a negative component determination section for determining presence/absence of a negative component of an event-related potential in the electroencephalogram signal in a zone from 100 ms to 300 ms from the same starting point; and an assessment section for evaluating whether the user has clearly aurally comprehended the presented speech sound or not based on the results of determination of presence/absence of the positive and negative components, respectively.

12 Claims, 19 Drawing Sheets

(56) References Cited

OTHER PUBLICATIONS

Kazuoki Kodera, "Hochoki Fittingu No Kangaekata" (or "Concept of Hearing Aid Fitting"), Shindan to Chiryosha, 1999, p. 172 and partial English translation.

R. Näätänen et al., "The N1 Wave of the Human Electric and Magnetic Response to Sound: A Review and an Analysis of the Component Structure", Psychophysiology, vol. 24, No. 4, pp. 375-425 (1987).

"Jishoukandrendeni (ERP) Manyuaru-P300 Wo Chushinni" (or "Event-Related Potential (ERP) Manual-mainly concerning P300"), edited by Kimitaka Kaga et al., Shinohara Shuppan Shinsha, 1995, p. 30 and partial English translation.

\* cited by examiner

|  |  | FLAT/DISTORTED | |
|---|---|---|---|
|  |  | FLAT | DISTORTED |
| SOUND PRESSURE | LARGE | LF CONDITION 60−65dB | LD CONDITION 60−65dB |
| | SMALL | SF CONDITION 40−45dB | SD CONDITION 40−45dB |

INCORRECT: 9.8%

CORRECT: 90.2%

INCORRECT: 40.1%

CORRECT: 59.8%

FIG.10A

|  |  | CONFIDENCE OF AURAL DISTINCTION | SPEECH SOUND INTELLIGIBILITY |
|---|---|---|---|
| POSITIVE COMPONENT @Pz | NO | HIGH | O (CLEAR) |
| | YES | LOW | △ (UNCLEAR) |

FIG.10B

|  |  | RESULT OF SOUND PRESSURE LEVEL DETERMINATION | CAUSE OF UNCLEARNESS |
|---|---|---|---|
| NEGATIVE COMPONENT @Pz | YES | SUFFICIENT SOUND PRESSURE | INSUFFICIENT GAIN OF CONSONANT FREQUENCY |
| | NO | INSUFFICIENT SOUND PRESSURE | INSUFFICIENT OVERALL GAIN |

*FIG.14*

| SPEECH SOUND | AUDIO FILE | CONSONANT LABEL | GROUP | | |
|---|---|---|---|---|---|
| | | | ROUGH CATEGORY | MEDIUM CATEGORY | FINE CATEGORY |
| a | a.wav | - | 0 | — | — |
| i | i.wav | - | 0 | — | — |
| u | u.wav | - | 0 | — | — |
| e | e.wav | - | 0 | — | — |
| o | o.wav | - | 0 | — | — |
| ka | ka.wav | k | 1 | 2 | — |
| sa | sa.wav | s | 1 | 1 | — |
| ta | ta.wav | t | 1 | 2 | — |
| na | na.wav | n | 2 | 2 | 1 |
| ha | ha.wav | h | 1 | 2 | — |
| ma | ma.wav | m | 2 | 2 | 1 |
| ya | ya.wav | y | 2 | 1 | — |
| ra | ra.wav | r | 2 | 1 | — |
| wa | wa.wav | w | 2 | 1 | — |
| ga | ga.wav | g | 2 | 2 | 2 |
| za | za.wav | z | 2 | 2 | 2 |
| da | da.wav | d | 2 | 2 | 2 |
| ba | ba.wav | b | 2 | 2 | 2 |
| ... | ... | ... | ... | ... | ... |

71 → (pointing to "ta" row)

FIG.15A

| SPEECH SOUND | INTELLIGIBILITY ASSESSMENT | CAUSE OF UNCLEARNESS |
|---|---|---|
| a | ○ | - |
| i | ○ | - |
| u | ○ | - |
| e | ○ | - |
| o | ○ | - |
| ka | ○ | - |
| sa | ○ | - |
| ta | ○ | - |
| na | △ | INSUFFICIENT OVERALL GAIN |
| ha | ○ | - |
| ma | △ | INSUFFICIENT OVERALL GAIN |
| ya | ○ | - |
| ra | △ | INSUFFICIENT OVERALL GAIN |
| wa | ○ | - |
| ga | ○ | - |
| za | ○ | - |
| da | △ | INSUFFICIENT OVERALL GAIN |
| ba | ○ | - |
| ... | ... | ... |

FIG.15B

| SPEECH SOUND | INTELLIGIBILITY ASSESSMENT | CAUSE OF UNCLEARNES |
|---|---|---|
| a | ○ | - |
| i | ○ | - |
| u | ○ | - |
| e | ○ | - |
| o | ○ | - |
| ka | ○ | - |
| sa | ○ | - |
| ta | ○ | - |
| na | △ | INSUFFICIENT GAIN OF CONSONANT FREQUENCY |
| ha | ○ | - |
| ma | △ | INSUFFICIENT GAIN OF CONSONANT FREQUENCY |
| ya | ○ | - |
| ra | △ | INSUFFICIENT GAIN OF CONSONANT FREQUENCY |
| wa | ○ | - |
| ga | ○ | - |
| za | ○ | - |
| da | △ | INSUFFICIENT GAIN OF CONSONANT FREQUENCY |
| ba | ○ | - |
| ... | ... | ... |

FIG.17

| WORD | INTELLIGIBILITY ASSESSMENT | CAUSE OF UNCLEARNESS |
|---|---|---|
| sit | ○ | - |
| meet | ○ | - |
| get | ○ | - |
| cat | ○ | - |
| come | ○ | - |
| hot | ○ | - |
| law | ○ | - |
| book | ○ | - |
| blue | △ | INSUFFICIENT GAIN OF CONSONANT FREQUENCY |
| urge | ○ | - |
| star | △ | INSUFFICIENT GAIN OF CONSONANT FREQUENCY |
| page | ○ | - |
| sky | △ | INSUFFICIENT SOUND PRESSURE |
| join | ○ | - |
| now | ○ | - |
| home | ○ | - |
| here | △ | INSUFFICIENT GAIN OF CONSONANT FREQUENCY |
| care | ○ | - |
| ... | ... | ... |

FIG.20A

| SPEECH SOUND | INTELLIGIBILITY ASSESSMENT | CAUSE OF UNCLEARNESS |
|---|---|---|
| a | ○ | - |
| ka | ○ | - |
| sa | △ | INSUFFICIENT OVERALL GAIN |
| ta | ○ | - |
| na | △ | INSUFFICIENT OVERALL GAIN |
| ha | ○ | - |
| ma | △ | INSUFFICIENT OVERALL GAIN |
| ya | ○ | - |
| ra | △ | INSUFFICIENT OVERALL GAIN |
| wa | ○ | - |
| ga | ○ | - |
| za | ○ | - |
| da | △ | INSUFFICIENT OVERALL GAIN |
| ba | ○ | - |
| ... | ... | ... |

FIG.20B

| SPEECH SOUND | INTELLIGIBILITY ASSESSMENT | CAUSE OF UNCLEARNESS |
|---|---|---|
| a | ○ | - |
| ka | ○ | - |
| sa | △ | INSUFFICIENT GAIN OF CONSONANT FREQUENCY |
| ta | ○ | - |
| na | ○ | - |
| ha | ○ | - |
| ma | ○ | - |
| ya | ○ | - |
| ra | ○ | - |
| wa | ○ | - |
| ga | ○ | - |
| za | ○ | - |
| da | ○ | - |
| ba | ○ | - |
| ... | ... | ... |

*FIG.20C*

| SPEECH SOUND | INTELLIGIBILITY ASSESSMENT | CAUSE OF UNCLEARNESS |
|---|---|---|
| a | ○ | - |
| ka | ○ | - |
| sa | ○ | - |
| ta | ○ | - |
| na | ○ | - |
| ha | ○ | - |
| ma | ○ | - |
| ya | ○ | - |
| ra | ○ | - |
| wa | ○ | - |
| ga | ○ | - |
| za | ○ | - |
| da | ○ | - |
| ba | ○ | - |
| ... | ... | ... |

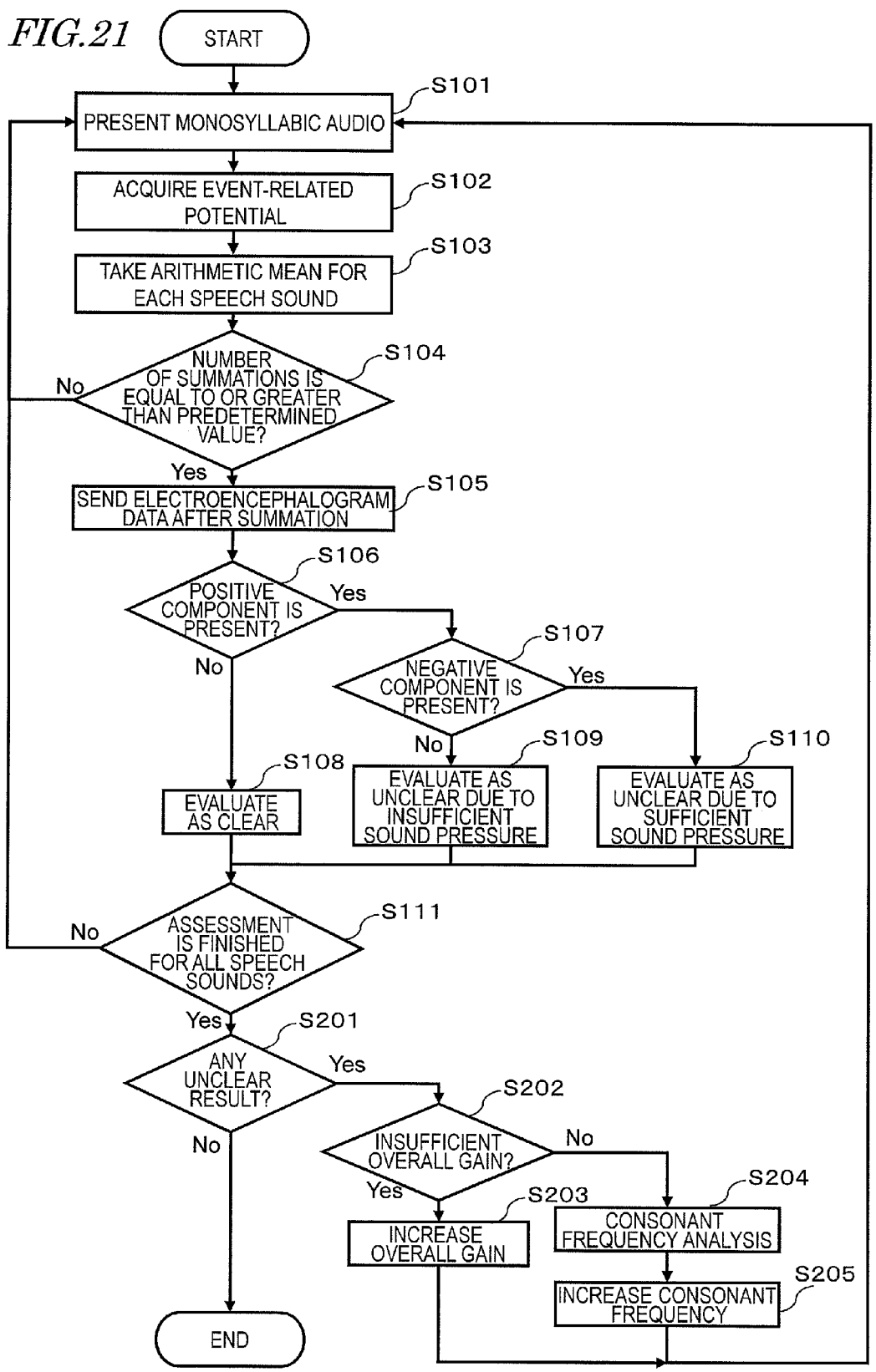

SPEECH SOUND INTELLIGIBILITY ASSESSMENT SYSTEM, AND METHOD AND PROGRAM THEREFOR

This is a continuation of International Application No. PCT/JP2011/000006, with an international filing date of Jan. 5, 2011, which claims priority of Japanese Patent Application No. 2010-017207, filed on Jan. 28, 2010, the contents of which are hereby incorporated by reference.

BACKGROUND OF THE INVENTION

1. Field of the Invention

The present invention relates to a technique for evaluating whether a speech sound has been aurally comprehended or not. More specifically, the present invention relates to a speech sound intelligibility assessment system for evaluating the degree as to how well a user has aurally comprehend a speech sound for the "fitting" of a hearing aid or the like to provide a sound of appropriate loudness for each individual user by adjusting the amount of amplification of sounds with respect to each frequency.

2. Description of the Related Art

In recent years, people suffering from presbycusis are increasing in number due to the aging society. Moreover, even among the young, due to increased opportunities for listening to loud music for long hours as well as other influences, there is an increasing number of people suffering from hypacusia associated with acoustic traumas (headphone-induced hearing loss).

Moreover, due to the downsizing and improved performance of hearing aids, users feel less of a psychological barrier against wearing hearing aids. Thus, there is an increasing number of users who use hearing aids.

A hearing aid is a device for compensating for the deteriorated hearing of a user by increasing the signal amplitude of sounds of specific frequencies, among sounds of various frequencies that compose sounds that are difficult for the user to aurally distinguish. The purpose of wearing a hearing aid is to improve conversational aural distinction abilities. The amount of sound amplification which a user desires in a hearing aid varies depending on the level of deterioration in the hearing of the user. Therefore, before beginning use of a hearing aid, "fitting" is required for adjusting the amount of sound amplification in accordance with the hearing of each user.

"Fitting" is performed in such a manner that the output sound pressure (i.e. fluctuations in air pressure that are perceivable as a sound) from a hearing aid is at a sound pressure level that is felt comfortable to a user (most comfortable level; hereinafter abbreviated as "MCL") for each frequency. If fitting is not appropriately done, e.g., the amount of amplification is insufficient, then sounds may not be heard sufficiently. If the amplification is excessive, the user may feel that it is too loud. In either case, problems such as inability to use the hearing aid for long periods of time will occur.

Fitting is generally performed based on each user's audiogram. An "audiogram" is a result of evaluating the smallest sound pressure of a pure tone being heard; for example, a diagram in which, for each of a number of sounds of different frequencies, the smallest sound pressure level (decibel value) that the user can aurally comprehend is plotted against frequency (e.g., 250 Hz, 500 Hz, 1000 Hz, 2000 Hz, 4000 Hz).

In order to perform fitting, it is necessary to generate an audiogram for each user first. Then, based on the resultant audiogram that is generated, fitting is performed based on a fitting theory for estimating an MCL for each user.

Currently, however, there is no one established fitting method that can determine an optimum amount of sound amplification with respect to any and every user for improving the conversational intelligibility in aural distinction from his or her audiogram alone. Possible reasons are, for example: an audiogram is not in one-to-one correspondence with a conversational aural distinction ability; a person suffering from hypacusia has a narrow range of sound pressure that is felt to him or her as an appropriate loudness; and so on.

Therefore, in order to evaluate the degree of fitting, a speech sound intelligibility assessment is needed. A "speech sound intelligibility assessment" (speech discriminability assessment) is an assessment as to whether a speech sound has actually been aurally comprehend or not, and is an assessment of aural distinction ability as to whether a monosyllabic speech sound has been aurally comprehended or not. A monosyllabic speech sound means either a single vowel or a combination of a consonant and a vowel (e.g., "あ (a)"/"だ (da)"/"し (shi)"). Since the purpose of wearing a hearing aid is aural distinction in conversations, assessment results of speech sound intelligibility are considered to better reflect hearing in conversations.

In Japan, speech sound intelligibility assessment has conventionally been performed through the following procedure ("HOCHOKI FITTINGU NO KANGAEKATA (or "Concept of Hearing Aid Fitting") Kazuoki KODERA, Shindan To Chiryosha, 1999, p. 166). First, by using the 57S list (50 monosyllables) or the 67S list (20 monosyllables) proposed by the Japan Audiological Society, a user is allowed to hear a monosyllabic speech sound via oral presentation or CD reproduction. Next, through oral explanation, writing, or other methods, the user is asked to answer which speech sound he or she has aurally comprehended the presented speech sound to be. Then, an evaluator matches the answers against the list in order to calculate a correctness rate, which is a rate of monosyllabic speech sounds that have been correctly aurally comprehended among all monosyllabic speech sounds.

However, in the aforementioned assessment method, the user is required to make answers via oral explanation or writing, and the evaluator needs to determine the correctness of the user's answers through manual labor. Thus, this test presents a large burden, and is time-consuming, on the part of the user and the evaluator.

Therefore, for example, Japanese Laid-Open Patent Publication No. 9-038069 discloses a speech sound intelligibility assessment method which, in order to reduce the burden of the evaluator, employs a personal computer (PC) to automatically perform correctness determination. Specifically, Japanese Laid-Open Patent Publication No. 9-038069 proposes a method in which monosyllabic speech sounds are presented in audio form to a user by using a PC; the user is asked to answer with the click of a mouse or by touching a pen to the display; the answers are received as inputs to the PC; and correctness determinations as to the presented audios and answer inputs are automatically made. Since answer inputs are received with a mouse click or a pen touch, there is no need for the evaluator to analyze and distinguish the user's answers (which are given by oral explanation or writing), whereby the trouble of the evaluator is reduced.

Moreover, for example, Japanese Laid-Open Patent Publication No. 6-114038 discloses a speech sound intelligibility assessment method in which, after audio presentation, possible choices of speech sounds are presented in the form of text characters, thus reducing the user's burden of making answer inputs. In Japanese Laid-Open Patent Publication No.

6-114038, choices are limited to only a small number so that the relevant speech sound can be found among the small number of characters, whereby the user's trouble of finding the character is reduced. Also in Japanese Laid-Open Patent Publication No. 6-114038, a PC is used to receive answer inputs, thus reducing the evaluator's burden.

However, in the speech sound intelligibility assessment methods described in Japanese Laid-Open Patent Publication No. 9-038069 and Japanese Laid-Open Patent Publication No. 6-114038, the user needs to make answer inputs, and an answer-inputting operation still exists, thus presenting a burden on the user. In particular, it is presumably not easy for people suffering from hypacusia or elderly people who are unaccustomed to working on a PC to make answer inputs with a mouse click or a pen touch. There has also been a possibility that the test may be time-consuming, or the wrong monosyllable matrix may be inadvertently selected through a manipulation mistake, in which case the speech sound intelligibility may not be correctly evaluated. Moreover, although the assessment result of each speech sound is indicated in the two values of clear or not clear (e.g., indicating clear or "A" indicating not clear), it has not been possible to identify causes of unclearness. This has hindered application to specific fitting procedures.

An objective of the present invention is to realize a speech sound intelligibility assessment system in which the user does not need to perform cumbersome answer-inputting, and which identifies causes of unclearness.

SUMMARY OF THE INVENTION

A speech sound intelligibility assessment system according to the present invention comprises: a speech sound database retaining a plurality of speech sounds; a presented-speech sound control section for determining a speech sound to be presented by referring to the speech sound database; an output section for presenting the determined speech sound to a user; a biological signal measurement section for measuring an electroencephalogram signal of the user; a positive component determination section for determining presence or absence of a positive component of an event-related potential in the electroencephalogram signal in a zone from 600 ms to 800 ms from a starting point, the starting point being a point in time at which the output section presents a speech sound; a negative component determination section for determining presence or absence of a negative component of an event-related potential in the electroencephalogram signal in a zone from 100 ms to 300 ms from a starting point, the starting point being a point in time at which the output section presents a speech sound; and a speech sound intelligibility assessment section for evaluating whether the user has clearly aurally comprehended the presented speech sound or not, based on a result of determination as to presence or absence of the positive component acquired from the positive component determination section and a result of determination as to presence or absence of the negative component acquired from the negative component determination section.

The speech sound intelligibility assessment section may make an evaluation that the user has clearly aurally comprehended the presented speech sound when the result of determination by the positive component determination section indicates that the positive component is absent; make an evaluation that the user has not clearly aurally comprehended the presented speech sound due to an insufficient overall sound pressure when the result of determination by the positive component determination section indicates that the positive component is present and the result of determination by the negative component determination section indicates that the negative component is absent; or make an evaluation that the user has not clearly aurally comprehended the presented speech sound due to an insufficient sound pressure of a consonant frequency when the result of determination by the positive component determination section indicates that the positive component is present and the result of determination by the negative component determination section indicates that the negative component is present.

The positive component determination section may compare between a predetermined threshold value and a zone average potential of an event-related potential in a zone from 600 ms to 800 ms from a starting point, the starting point being a point in time at which the output section presents a speech sound, and determine that the positive component is present when the zone average potential is equal to or greater than the threshold value, or determine that the positive component is absent when the zone average potential is smaller than the threshold value.

The negative component determination section may compare between a predetermined threshold value and an absolute value of a negative peak value of an event-related potential in a zone from 100 ms to 300 ms from a starting point, the starting point being a point in time at which the output section presents a speech sound, and determine that the negative component is present when the absolute value of the peak value is equal to or greater than the threshold value, or determine that the negative component is absent when the absolute value of the peak value is smaller than the threshold value.

In the speech sound database, a speech sound type, consonant information type, and a group concerning probability of confusion may be associated with each of the plurality of speech sounds retained therein.

The speech sound intelligibility assessment system may further comprise an event-related potential processing section for referring to association between the speech sound type, the consonant information type, and the group concerning probability of confusion stored in the speech sound database, and generating electroencephalogram data by taking an arithmetic mean of event-related potentials corresponding to the presented speech sound, with respect to each of the speech sound type, the consonant information type, and the group concerning probability of confusion.

The output section may present a plurality of speech sounds; the positive component determination section and the negative component determination section may receive electroencephalogram data obtained by taking an arithmetic mean of event-related potentials with respect to each speech sound type, each consonant type, or each group concerning probability of confusion in connection with the presented plurality of speech sounds; based on the electroencephalogram data, the positive component determination section may determine presence or absence of the positive component of the event-related potential with respect to each speech sound type, each consonant type, or each group concerning probability of confusion; and based on the electroencephalogram data, the negative component determination section may determine presence or absence of the negative component of the event-related potential with respect to each speech sound type, each consonant type, or each group concerning probability of confusion.

The speech sound database may further retain gain information defining a gain for each of frequency bands concerning the plurality of speech sounds, and the speech sound intelligibility assessment system may further comprise: a stimulation speech sound gain adjustment section for, with respect to any speech sound that is evaluated by the speech sound intelligibility assessment section as not being clearly aurally comprehended by the user due to an insufficient overall sound pressure, updating the frequency-by-frequency gain information concerning speech sounds that is retained in the speech sound database so as to increase the gain for the entire frequency band, and with respect to any speech sound that is evaluated by the speech sound intelligibility assessment section as not being clearly aurally comprehended by the user due to an insufficient sound pressure of a consonant frequency, calculating a consonant frequency band of the speech sound and updating the frequency-by-frequency gain information concerning speech sounds that is retained in the speech sound database so as to increase the gain for the consonant frequency band.

A speech sound intelligibility assessment method according to the present invention comprises the steps of: providing a speech sound database retaining a plurality of speech sounds; determining a speech sound to be presented by referring to the speech sound database; presenting the determined speech sound to a user; measuring an electroencephalogram signal of the user; determining presence or absence of a positive component of an event-related potential in the electroencephalogram signal in a zone from 600 ms to 800 ms from a starting point, the starting point being a point in time at which the output section presents a speech sound; determining presence or absence of a negative component of an event-related potential in the electroencephalogram signal in a zone from 100 ms to 300 ms from a starting point, the starting point being a point in time at which the output section presents a speech sound; and evaluating whether the user has clearly aurally comprehended the presented speech sound or not based on a result of determination of presence or absence of the positive component and a result of determination of presence or absence of the negative component.

The evaluating step may make an evaluation that the user has clearly aurally comprehended the presented speech sound when a result of determination of presence or absence of the positive component indicates that the positive component is absent; make an evaluation that the user has not clearly aurally comprehended the presented speech sound due to an insufficient overall sound pressure when a result of determination of presence or absence of the positive component indicates that the positive component is present and a result of determination of presence or absence of the negative component indicates that the negative component is absent; or make an evaluation that the user has not clearly aurally comprehended the presented speech sound due to an insufficient sound pressure of a consonant frequency when a result of determination of presence or absence of the positive component indicates that the positive component is present and a result of determination of presence or absence of the negative component indicates that the negative component is present.

A computer program according to the present invention is to be executed by a computer mounted in a speech sound intelligibility assessment system including a speech sound database retaining a plurality of speech sounds, wherein the computer program causes the computer in the speech sound intelligibility assessment system to execute the steps of: determining a speech sound to be presented by referring to the speech sound database; presenting the determined speech sound to a user; measuring an electroencephalogram signal of the user; determining presence or absence of a positive component of an event-related potential in the electroencephalogram signal in a zone from 600 ms to 800 ms from a starting point, the starting point being a point in time at which the output section presents a speech sound; determining presence or absence of a negative component of an event-related potential in the electroencephalogram signal in a zone from 100 ms to 300 ms from a starting point, the starting point being a point in time at which the output section presents a speech sound; and evaluating a speech sound intelligibility indicating whether the user has clearly aurally comprehended the presented speech sound or not based on a result of determination of presence or absence of the positive component and a result of determination of presence or absence of the negative component.

The evaluating step may make an evaluation that the user has clearly aurally comprehended the presented speech sound when a result of determination of presence or absence of the positive component indicates that the positive component is absent; make an evaluation that the user has not clearly aurally comprehended the presented speech sound due to an insufficient overall sound pressure when a result of determination of presence or absence of the positive component indicates that the positive component is present and a result of determination of presence or absence of the negative component indicates that the negative component is absent; or make an evaluation that the user has not clearly aurally comprehended the presented speech sound due to an insufficient sound pressure of a consonant frequency when a result of determination of presence or absence of the positive component indicates that the positive component is present and a result of determination of presence or absence of the negative component indicates that the negative component is present.

A speech sound intelligibility assessment apparatus according to the present invention comprises: a presented-speech sound control section for determining a speech sound to be presented by referring to a speech sound database retaining a plurality of speech sounds; a positive component determination section for determining presence or absence of a positive component of an event-related potential in an electroencephalogram signal of a user measured by a biological signal measurement section in a zone from 600 ms to 800 ms from a starting point, the starting point being a point in time at which the speech sound is presented; a negative component determination section for determining presence or absence of a negative component in an event-related potential in the electroencephalogram signal in a zone from 100 ms to 300 ms from a starting point, the starting point being a point in time at which a speech sound is presented by an output section; and a speech sound intelligibility assessment section for evaluating whether the user has clearly aurally comprehended the presented speech sound or not based on a result of determination as to presence or absence of the positive component acquired from the positive component determination section and a result of determination as to presence or absence of the negative component acquired from the negative component determination section.

A method of operating a speech sound intelligibility assessment system according to the present invention comprises: a step where a presented-speech sound control section determines a speech sound to be presented by referring to a speech sound database retaining a plurality of speech sounds; a step where an output section presents the determined speech sound to a user; a step where an electroencephalogram measurement section measures an electroencephalogram signal of the user; a step where a positive component determination section determines presence or absence of a positive component of an event-related potential in the electroencephalogram signal in a zone from 600 ms to 800 ms from a starting point, the starting point being a point in time at which the output section presents a speech sound; a step where a negative component determination section determines presence or absence of a negative component of an event-related potential in the electroencephalogram signal in a zone from 100 ms to 300 ms from a starting point, the starting point being a point in time at which the output section presents a speech sound; and a step where a speech sound intelligibility assessment section evaluates whether the user has clearly aurally comprehended the presented speech sound or not based on a result of determination of presence or absence of the positive component and a result of determination of presence or absence of the negative component.

Alternatively, the speech sound intelligibility assessment system comprises: a speech sound database retaining a plurality of speech sounds; a presented-speech sound control section for determining a speech sound to be presented by referring to the speech sound database; an output section for presenting the determined speech sound to a user; a biological signal measurement section for measuring an electroencephalogram signal of the user; a positive component determination section for determining presence or absence of a positive component of an event-related potential in the electroencephalogram signal in a zone from 600 ms to 800 ms from a starting point, the starting point being a point in time at which the output section presents a speech sound; a negative component determination section for determining presence or absence of a negative component of an event-related potential in the electroencephalogram signal in a zone from 100 ms to 300 ms from a starting point, the starting point being a point in time at which the output section presents a speech sound; and a speech sound intelligibility assessment section for evaluating whether the user has clearly aurally comprehended the presented speech sound or not, based on a result of determination as to presence or absence of the positive component acquired from the positive component determination section and a result of determination as to presence or absence of the negative component acquired from the negative component determination section; and a stimulation speech sound gain adjustment section for, when the positive component is absent and the negative component is absent, increasing the gain for the entire frequency band; or when the positive component is absent and the negative component is present, calculating a consonant frequency band of the speech sound and increasing the gain for the consonant frequency band.

According to one embodiment of the present invention, in accordance with the presence or absence of a positive component at a latency of about 700 ms and a negative component at a latency of about 200 ms of a user after an audio is presented, it is possible to make a speech sound intelligibility assessment and automatically identify whether the cause of unclearness is an insufficient sound pressure or not. Since the user does not need to perform cumbersome answer-inputting, both an evaluator and the user are allowed, with less burden, to make an assessment as to whether the user has clearly aurally comprehended the presented speech sound or not. Moreover, by determining whether the cause of unclearness is an insufficient sound pressure or not, a speech sound intelligibility assessment is realized which is easily applicable to a specific fitting procedure.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 10A is a diagram showing correspondence between presence or absence of a positive component and confidence of aural distinction and ease of hearing; FIG. 10B is a diagram, in the case of unclear aural distinction, showing correspondence between presence or absence of a negative component and results of sound pressure level determination and estimated causes of unclearness.

FIG. 14 is a diagram showing an example of a speech sound DB 71.

FIGS. 15A and 15B are diagrams showing exemplary results of speech sound intelligibility assessments by using a technique according to Embodiment 1.

FIG. 17 is a diagram showing exemplary assessment results for different monosyllabic words.

FIG. 20A is a diagram showing results of speech sound intelligibility assessment for a user when hearing audio stimulations which have been subjected to a gain adjustment based on predetermined initial characteristics;

FIG. 20B is a diagram showing exemplary results of speech sound intelligibility assessment made in a speech sound intelligibility assessment section 80 for a user when hearing audio stimulations which have been adjusted by adjustment method A; and FIG. 20C is a diagram showing exemplary results of speech sound intelligibility assessment for speech sounds which have been adjusted by adjustment method B.

FIG. 21 is a flowchart showing a processing procedure by the speech sound intelligibility system 200 according to Embodiment 2.

DETAILED DESCRIPTION OF PREFERRED EMBODIMENTS

Figure 1:
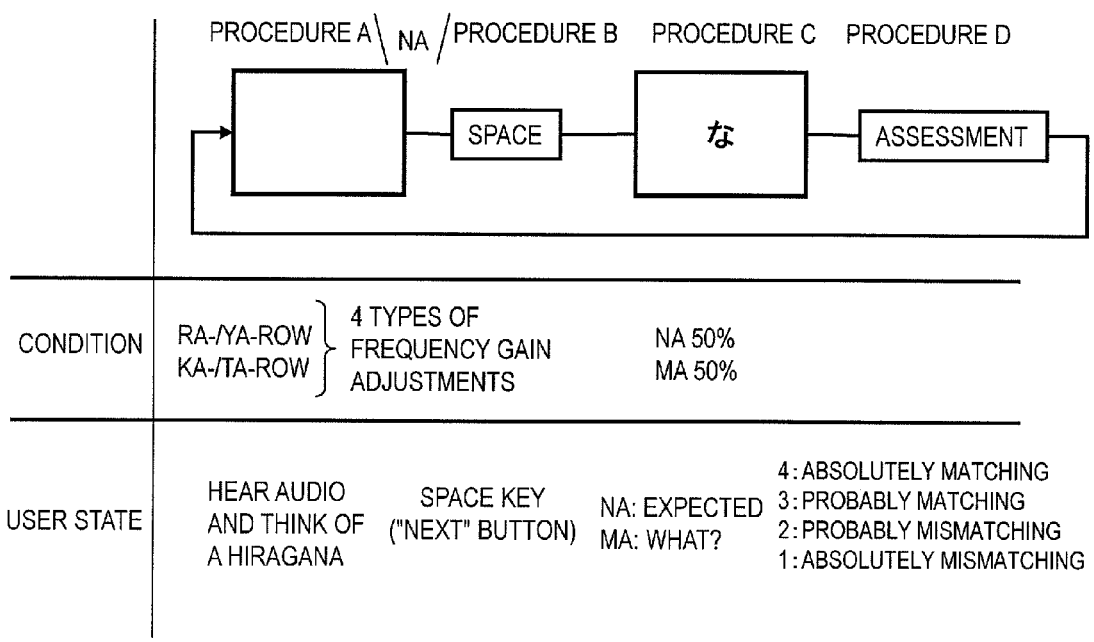
FIG. 1 is a diagram describing the experimental procedure of a behavioral experiment in outline.

Hereinafter, with reference to the attached drawings, embodiments of the speech sound intelligibility assessment system according to the present invention will be described.

A speech sound intelligibility assessment system according to the present invention is used for evaluating a speech sound intelligibility by utilizing an electroencephalogram. More specifically, the speech sound intelligibility assessment system is used for evaluating aural distinction concerning speech sounds on the premise of presenting a monosyllabic speech sound in the form of an audio and asking the user to aurally distinguish the audio, where an event-related potential of an electroencephalogram signal from a user is utilized as an index, based on the point of audio presentation as a starting point. In the present specification, to "present an audio" means to output an auditory stimulation (also referred to as an "audio stimulation"), e.g., outputting an audio through a loudspeaker. Note that the type of loudspeaker may be arbitrary. It may be a loudspeaker which is placed on the floor or on a stand, or may be the loudspeakers of a pair of headphones, so long as it is able to accurately present a designated sound pressure in order to correctly perform a speech sound intelligibility assessment.

The inventors have conducted the following two kinds of experiments to identify an electroencephalogram characteristic component(s) for realizing a speech sound intelligibility assessment which does not require answer inputs by a user.

First, a behavioral experiment was conducted for examining the relationship between confidence of aural distinction concerning audios and probability of confusion. As used herein, "confusion" means aurally comprehending a given sound to be a different sound. In the behavioral experiment, a monosyllabic speech sound(s) were presented in the form of an audio and a character (hiragana), and a user was asked to confirm whether the audio and the character were identical, who used a button to indicate his or her confidence of aural distinction concerning the audio. As a result, it was recognized that the probability of confusion is as low as 10% or less when the confidence of aural distinction concerning the audio is high, and that the probability of confusion is as high as about 40% when the confidence of aural distinction is low.

Next, the inventors conducted an experiment where, on the premise of presenting a monosyllabic speech sound in the form of an audio and asking a user to think of a speech sound corresponding to the audio, an event-related potential was measured based on the point of audio presentation as a starting point. Then, based on the confidence of aural distinction previously acquired through a behavioral experiment and the stimulation sound pressure being large or small, an arithmetic mean of the event-related potential was taken. It was thus found, in the event-related potential measured based on the point of presenting an audio stimulation as a starting point, that: (1) when the confidence of aural distinction for the audio is high, a positive component is induced at the parietal at a latency of about 700 ms, as compared to the case where the confidence of aural distinction for the audio is low; and (2) independently from the aforementioned positive component, the amplitude of a negative component at a latency of about 200 ms increases with an increase in the sound pressure level of the stimulation audio. As used herein, "positive component at a latency of about 700 ms" refers to a positive component which appears in a zone from 600 ms to 800 ms based on the point of presenting an audio stimulation as a starting point. A "negative component at a latency of about 200 ms" refers to a negative component which appears in a zone from 100 ms to 300 ms based on the point of presenting an audio stimulation as a starting point.

From the above recognition and findings, it has been found that: (1) a speech sound intelligibility can be evaluated on the basis of a confidence of aural distinction concerning audios, which can be determined from the presence or absence of a positive component in an event-related potential at a latency of 700 ms based on the point of audio presentation as a starting point; and (2) from the presence or absence of a negative component at a latency of about 200 ms, it is possible to identify whether the cause of unclearness was an insufficient sound pressure. Conventionally, a speech sound intelligibility assessment is made based only on whether a user's answer is correct or not. In contrast, the present approach realizes a detailed speech sound intelligibility assessment based on whether the user believes that he or she has aurally distinguished an audio or not.

These will be described in more detail below. Firstly, a behavioral experiment and an electroencephalogram measurement experiment which were conducted by the inventors in order to realize a speech sound intelligibility assessment which does not require answer inputs by a user will be described. Thereafter, as an embodiment, an outline of a speech sound intelligibility assessment apparatus for evaluating aural distinction concerning speech sounds, as well as a construction and operation of a speech sound intelligibility assessment system including the speech sound intelligibility assessment apparatus, will be described.

1. Behavioral Experiment

The inventors conducted a behavioral experiment in order to examine the relationship between confidence of aural distinction concerning audios and probability of confusion. Hereinafter, with reference to FIG. 1 to FIG. 3, the experimental setting and experimental results of the behavioral experiment conducted will be described.

Eleven undergraduate or graduate students with normal hearing participated in the experiment.

FIG. 1 shows the experimental procedure of the behavioral experiment in outline.

First, a monosyllabic audio was presented in procedure A. With reference to "HOCHOKI FITTINGU NO KANGAEKATA (or "Concept of Hearing Aid Fitting") (Kazuoki KODERA, Shindan To Chiryosha, 1999, p. 172), the audio to be presented was selected from among a pair of na- and ma-rows, a pair of ra- and ya-rows, and a pair of ka- and ta-rows, which are known to mutually induce mistakes in aural distinction.

Each experimental participant was instructed to think of a hiragana upon hearing the audio. Audios under four conditions were presented, with the frequency gain being modified so that the confidence of aural distinction would be diversified among participants with normal hearing. A "frequency gain" refers to a gain (i.e., a circuit gain or rate of amplification) for each of a number of frequency bands.

(1) LF (Large Flat) condition: the frequency gain was not modified because the audio had a large sound pressure and was easy to aurally distinguish. (2) SF (Small Flat) condition: the gain was decreased by 20 dB across the entire frequency band because the audio had a small sound pressure but was easy to aurally distinguish. (3) SD (Small Distorted) condition: the gain was gradually adjusted (decreased) to −50 dB because the audio had a small sound pressure and was difficult to aurally distinguish. (4) LD (Large Distorted) condition: the frequency gain was universally increased by 15 dB relative to the SD condition because the audio had a large sound pressure but was difficult to aurally distinguish.

Figures 2A, 2B:
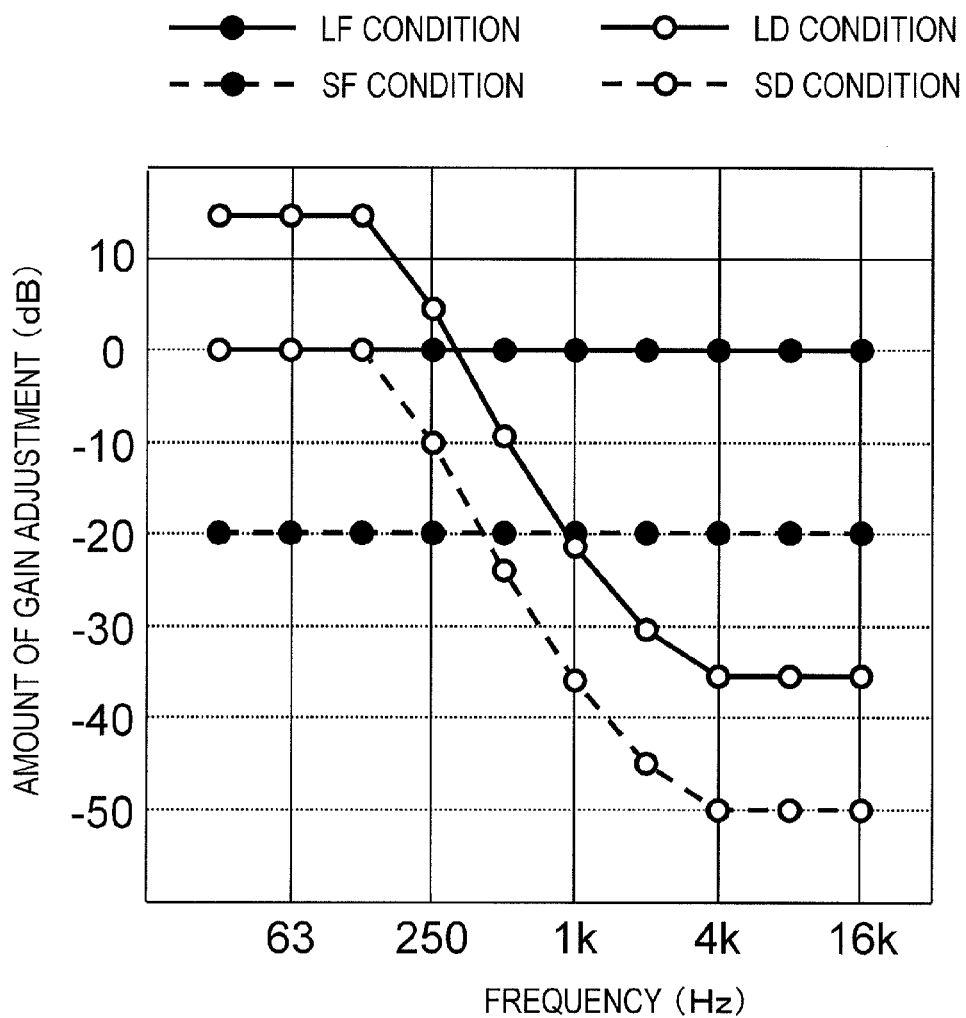
FIG. 2A is a diagram showing amounts of gain adjustment for different frequencies under each of four conditions.
FIG. 2B is a diagram showing sound pressure levels under the respective conditions, as measured with a sound-level meter.

FIG. 2A shows amounts of gain adjustment for different frequencies under each of conditions (1) to (4). The reason why the frequency gain for higher frequencies was decreased was in order to reproduce a typical pattern of hypacusia of elderly people, and to allow even a person with normal hearing to experience a similar hearing to the difficult hearing of elderly people suffering from hypacusia. FIG. 2B shows sound pressure levels under the respective conditions, as measured with a sound-level meter. It can be seen from FIG. 2B that the LF condition and the LD condition are characterized by similarly large sound pressures, and that the SF condition and the SD condition are characterized by similarly small sound pressures.

Next, in procedure B, the experimental participant was asked to press the SPACE key on the keyboard. Procedure B, which concerns a button pressing for being able to proceed to procedure C, was introduced in this experiment to allow the participant to experience the character stimulation of procedure C at his or her own pace. This button is also referred to as the "NEXT" button.

In procedure C, a hiragana character was presented on a display. The character matching the audio presented in procedure A was presented as a matching trial, and a hiragana not matching the audio was presented as a mismatching trial, both with a probability of 0.5. As each mismatching hiragana, a character in a different row from that of the audio was chosen, from within a pair of ra- and ya-rows or a pair of ka- and ta-rows (which are generally supposed to induce many mistakes in aural distinction), while the vowel was not changed. For example, if a hiragana "や (ya)" was presented in procedure A, then "や" was to be presented as a matching trial in procedure C, and "ら (ra)" was to be presented as a mismatching trial in procedure C.

Procedure D involves a button pressing (numbers 1 to 4 on the keyboard) for confirming how mismatching the audio presented in procedure A and the character presented in procedure C were to the participant. The participant was supposed to press "4" to express "absolutely matching", "3" to express "probably matching", to express "probably mismatching", and "1" to express "absolutely mismatching". If 4 or 1 was pressed during this button pressing, it means that, although the participants were diversified between correct and incorrect (as a result of confusion) in procedure C, they were confident in their aural distinction at the point of hearing the audio presented in procedure A. Similarly, if either 2 or 3 was pressed, it means that the participants were unconfident in their aural distinction of the audio.

In the experiment conducted, procedure A to procedure D described above was repeated 96 times (96 trials).

Figure 3:
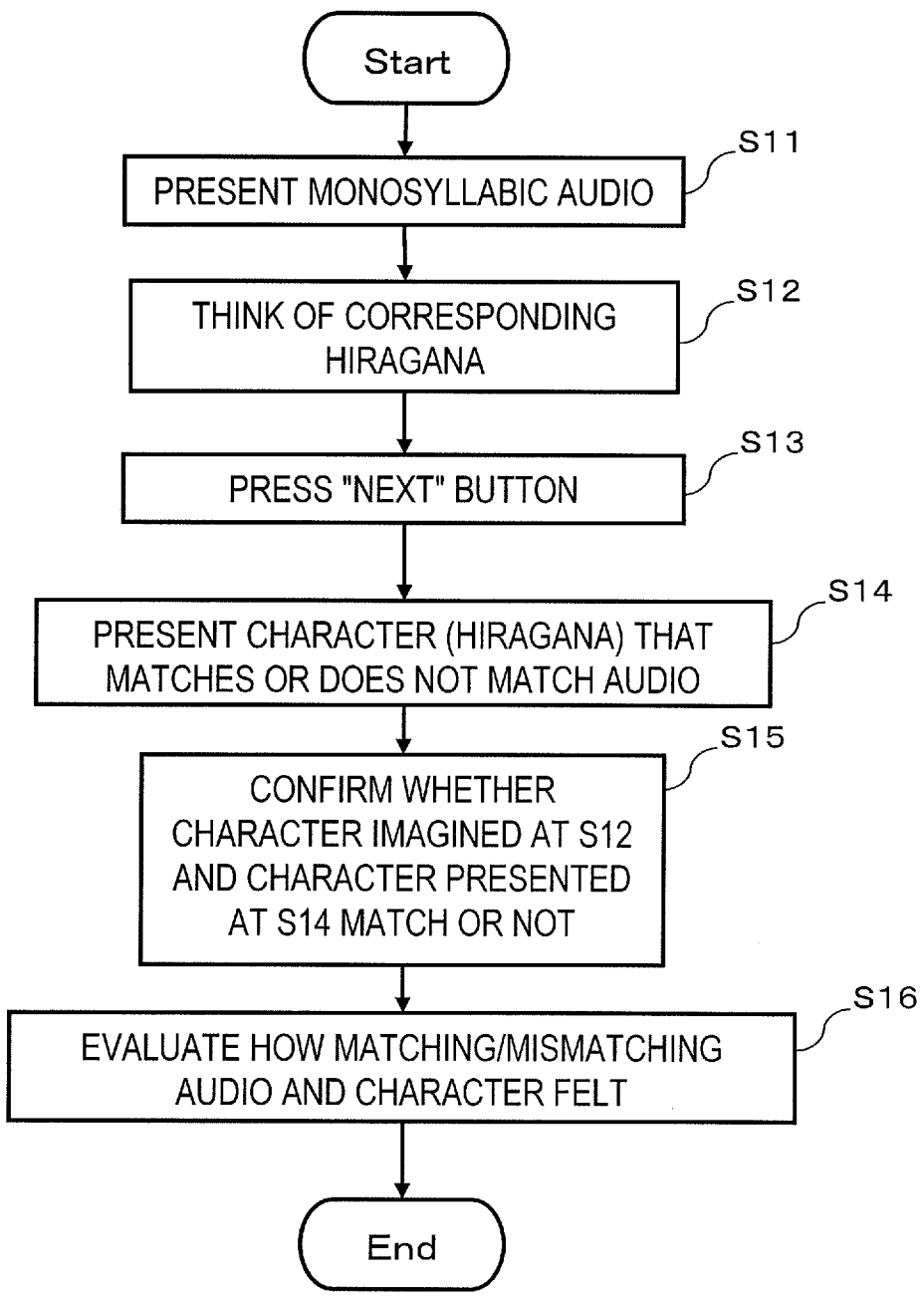
FIG. 3 is a flowchart showing a procedure corresponding to one trial.

FIG. 3 is a flowchart showing a procedure corresponding to one trial. In this flowchart, for ease of explanation, the operation of the apparatus and the operation of the experimental participant are both present.

step S11 is a step of presenting a monosyllabic audio to the experimental participant. The audio was presented under the four conditions of the LF condition, the SF condition, the LD condition, and the SD condition, these conditions being in random order (procedure A).

Step S12 is a step where the participant thinks of a corresponding hiragana upon hearing the monosyllabic audio.

Step S13 is a step where the participant presses the SPACE key as a "NEXT" button (procedure B).

Step S14 is a step of presenting on a display a hiragana character matching the audio or a hiragana character mismatching the audio, both with a 50% probability as reckoned from the execution of step S13 as the starting point (procedure C).

Step S15 is a step of confirming whether the hiragana which the participant thought of at step S12 matches the hiragana presented at step S14.

Step S16 is a step of answering how matching/mismatching they were felt to the participant at step S15, via number keys of 1 to 4 (procedure D).

The experimental results of the behavioral experiment are described below.

FIG. 4 shows degrees of confidence in aural distinction of audios by participants, as categorized based on results of button pressing, and correctness/incorrectness probabilities of button pressing. The degrees of confidence of aural distinction were categorized as follows. Any case where 4 (absolutely matching) or 1 (absolutely mismatching) was pressed was defined as a case with a "high" confidence of aural distinction. Out of all trials, the probability that the confidence was "high" was 82.3% (869 trials in 1056 trials). Any case where 3 (probably matching) or 2 (probably mismatching) was pressed was defined as a case with a "low" confidence of aural distinction. Out of all trials, the probability that the confidence was "low" was 17.7% (187 trials in 1056 trials). The correctness of button pressing was determined based on matching/mismatching between the audio and the character and the button that was pressed. The cases where 4 (absolutely matching) or 3 (probably matching) was pressed for a matching trial, or 1 (absolutely mismatching) or 2 (probably mismatching) for a mismatching trial were defined as "correct", whereas any other case was defined as "incorrect".

Figure 4A:
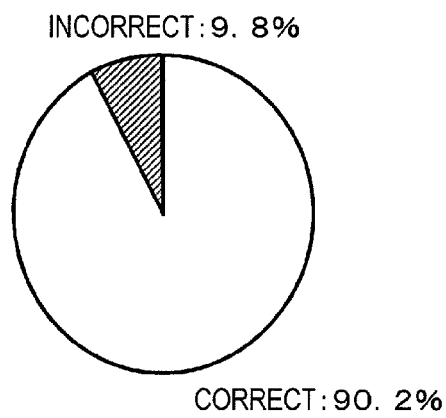
FIGS. 4A and 4B are diagrams showing degrees of confidence in aural distinction of audios by participants, as categorized based on results of button pressing, and correctness/incorrectness probabilities of button pressing.

FIG. 4A shows correctness/incorrectness results of button pressing in trials with high confidence of aural distinction. It can be seen that the correct button is selected in almost all trials (90.2%). This indicates that the audio is correctly aurally-distinguished when the confidence of aural distinction is high. Based on these results, it can be said that a high speech sound intelligibility assessment may be made when the confidence of aural distinction is high.

Figure 4B:
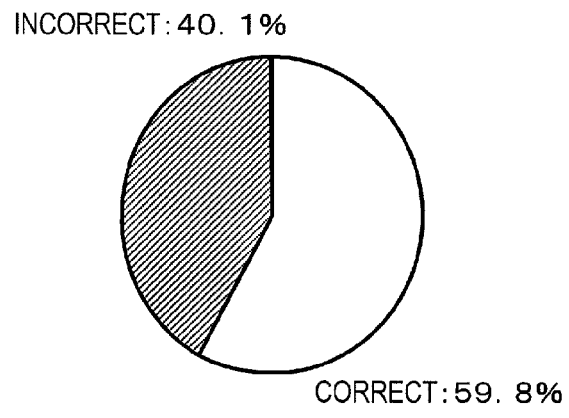

FIG. 4B shows correctness/incorrectness results of button pressing in trials with low confidence of aural distinction. It can be seen that there is a high probability that the wrong button was pressed (40.1%). This indicates that confusion is likely to occur when the confidence of aural distinction is low. Based on these results, it can be said that a low speech sound intelligibility assessment may be made when the confidence of aural distinction is low.

Note that each participant's probability of confusion was significantly high ($p<0.01$) when the confidence of aural distinction was high.

Thus, through the behavioral experiment, a clear possibility has been indicated that speech sound intelligibility assessment can be realized based on a user's confidence of aural distinction concerning audios. Therefore, if confidence of aural distinction can be measured by a method other than button pressing, a speech sound intelligibility assessment not involving any answer inputs can be realized based on that index. Paying attention to the event-related potential of the electroencephalogram, the inventors have conducted an electroencephalogram measurement experiment to examine whether there exists any component that reflects differences in confidence of aural distinction concerning audios. Hereinafter, the electroencephalogram measurement experiment will be described.

2. Electroencephalogram Measurement Experiment

In order to examine a relationship between the confidence of aural distinction concerning audios and sound pressure levels of audio stimulations and the event-related potential after audio presentation, the inventors have conducted an electroencephalogram measurement experiment. Hereinafter, with reference to FIG. 5 to FIG. 9, the experimental setting and experimental results of the electroencephalogram measurement experiment conducted will be described.

The experimental participants were the same eleven undergraduate or graduate students in the behavioral experiment.

Figure 5:
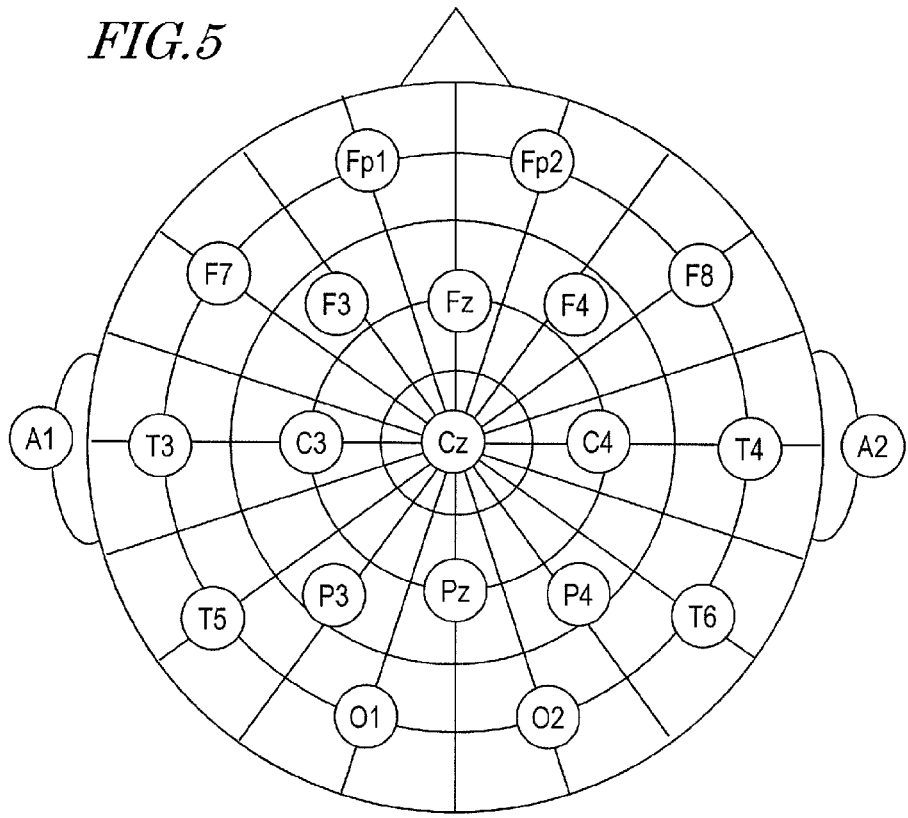
FIG. 5 is a diagram showing electrode positions according to the International 10-20 system.

Each electroencephalogram was recorded from electrodes placed at the Fz, Cz, Pz, C3, and C4 positions (International 10-20 system) on the scalp, on the basis of the right mastoid. A "mastoid" is a protrusion of the cranium below the hind root of an ear. FIG. 5 is a diagram showing the electrode positions according to the International 10-20 system. The sampling frequency was 200 Hz, and the time constant was 1 second. It was subjected to a 1 to 6 Hz digital band-pass filter off-line. As an event-related potential in response to an audio presentation, a waveform from −200 ms to 1000 ms was cut out based on the point of audio presentation as a starting point. An arithmetic mean of the event-related potential was taken under each condition (LF/SF/LD/SD) in the above-described behavioral experiment.

Figure 6:
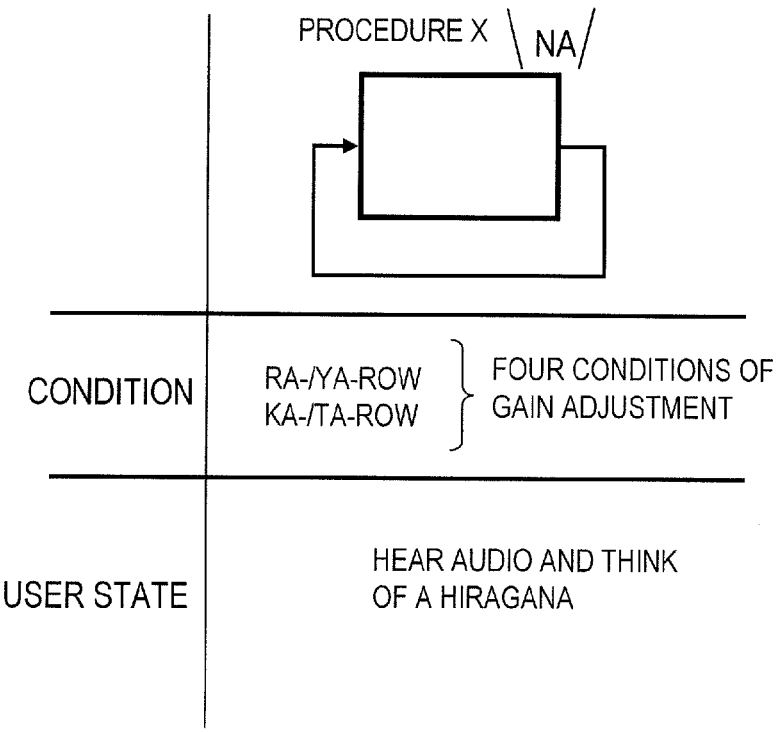
FIG. 6 is a diagram showing the experimental procedure of an electroencephalogram measurement experiment in outline.

FIG. 6 shows the experimental procedure of the electroencephalogram measurement experiment in outline.

In procedure X, a monosyllabic audio was presented. Similarly to the behavioral experiment, the stimulation speech sound was selected from among ra-row/ya-row, or ka-row/ta-row. Each experimental participant was instructed to think of a hiragana upon hearing the audio. Moreover, audios under the following four conditions were presented, with the frequency gain being modified so that the confidence of aural distinction and the sound pressure level of the stimulation audio would vary among the participants with normal hearing.

(1) LF (Large Flat) condition: the frequency gain was not modified because the audio had a large sound pressure and was easy to aurally distinguish. (2) SF (Small Flat) condition: the gain was decreased by 20 dB across the entire frequency band because the audio had a small sound pressure but was easy to aurally distinguish. (3) SD (Small Distorted) condition: the gain was gradually adjusted (decreased) to −50 dB because the audio had a small sound pressure and was difficult to aurally distinguish. (4) LD (Large Distorted) condition: the gain was universally increased by 15 dB relative to the SD condition because the audio had a large sound pressure but was difficult to aurally distinguish. FIG. 2A shows frequency amounts of gain adjustment under the four conditions; and FIG. 2B shows sound pressure levels under the four conditions as measured with a sound-level meter.

In the experiment, the above procedure X was repeated 192 times, in two blocks each containing 96 times.

Figure 7:
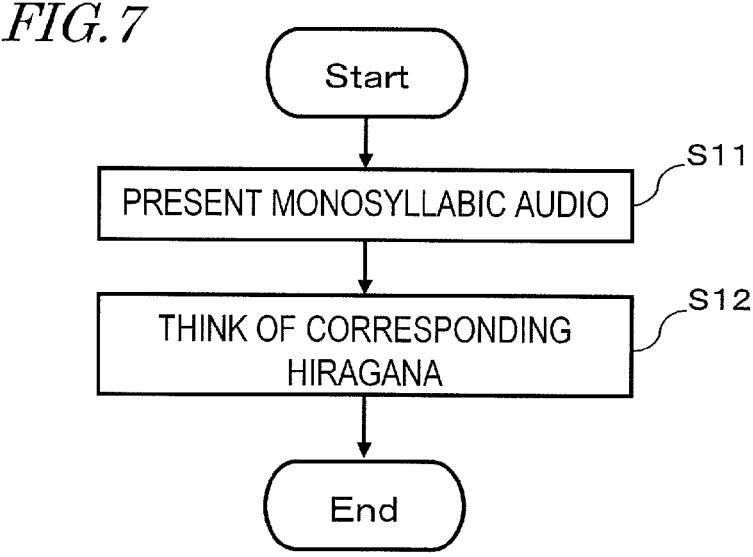
FIG. 7 is a flowchart showing a procedure corresponding to one trial.

FIG. 7 is a flowchart showing a procedure corresponding to one trial. Any block that has a like counterpart in FIG. 3 will be denoted by a like reference numeral, and the description thereof will be omitted. The difference from FIG. 3 is that step S13 to step S16 are omitted, so that each experimental participant is not required to make any explicit action.

Hereinafter, experimental results of the electroencephalogram measurement experiment will be described.

Figure 8:
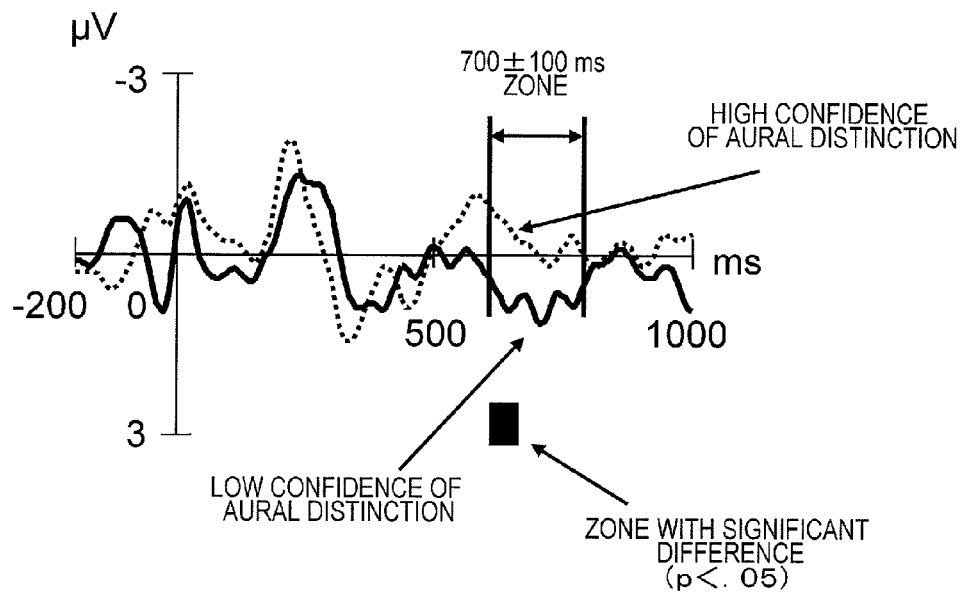
FIG. 8 is a diagram showing waveforms of event-related potentials at Pz, based on a point of presenting an audio as a starting point, where total arithmetic means are taken based on confidence of aural distinction.

FIG. 8 shows event-related potentials at Pz, based on the point of audio presentation as a starting point, where total arithmetic means are taken based on confidence of aural distinction. An arithmetic mean of the event-related potential was taken based on the confidence of aural distinction with respect to each speech sound and each participant, under each condition (LF/SF/LD/SD) in the above-described behavioral experiment. In FIG. 8, the horizontal axis represents time in units of ms, whereas the vertical axis represents potential in units of μV. As is clear from the scales shown in FIG. 8, the lower direction in the graph corresponds to plus (positive), and the upper direction corresponds to minus (negative). As for the baseline, an average potential from −200 ms to 0 ms is adjusted to zero.

In FIG. 8, the broken line represents an arithmetic mean waveform of the event-related potential at the electrode position Pz in the case where the confidence of aural distinction was high in the behavioral experiment, and the solid line represents that of the case where the confidence of aural distinction was low. It can be seen from FIG. 8 that, as compared to the broken line representing a high confidence of aural distinction, a mild positive component appears at a latency of about 700 ms in the solid line representing a low confidence of aural distinction. As a result of performing a t-test for every sampling from 0 ms to 1000 ms, the time slot where a significant difference due to the aforementioned difference in confidence of aural distinction lasted for 20 ms or more was from 608 ms to 668 ms.

An average potential in a zone from 600 ms to 800 ms (zone average potential) of each participant (centered around the latency of 700 ms, which corresponds to a positive potential peak) was −0.24 μV in the case of a high confidence of aural distinction, and 0.74 μV in the case of a low confidence. Through a t-test of the zone average potential, it was found that the zone average potential was significantly large in the case of a low confidence of aural distinction ($p<0.05$).

Figure 9:
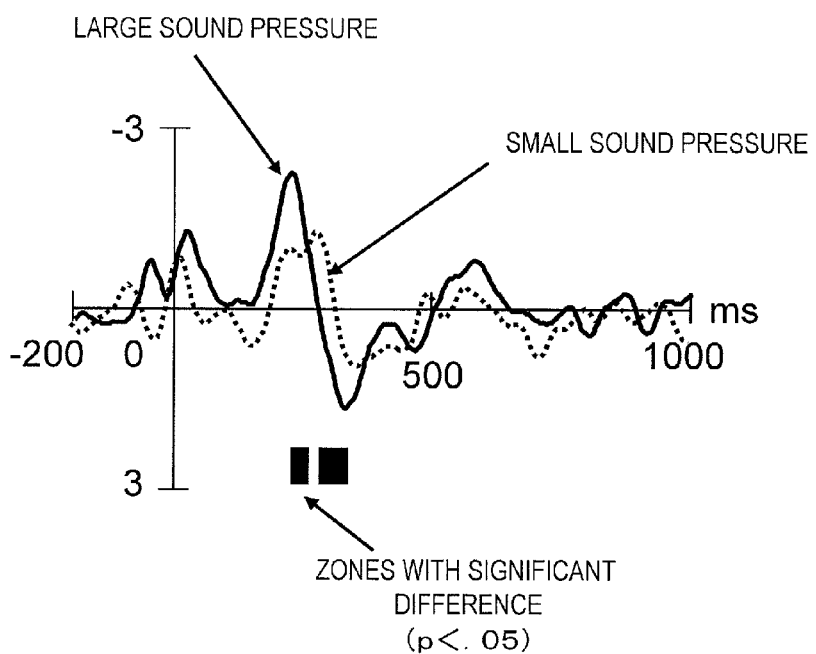
FIG. 9 is a diagram showing waveforms of event-related potentials at Pz, based on a point of presenting an audio as a starting point, where arithmetic means are taken for different sound pressure levels of audio stimulations.

FIG. 9 shows waveforms of event-related potentials at Pz, based on a point of audio presentation as a starting point, where arithmetic means are taken for different sound pressure levels of audio stimulations. More specifically, each user's degrees of confidence of aural distinction were pooled, and an arithmetic mean of the event-related potential when audio stimulations were presented under the LF/LD conditions, where the sound pressure level was as large as 60 dB to 65 dB, was derived, and an arithmetic mean of the event-related potential when audio stimulations were presented under the SF/SD conditions, where the sound pressure level was as small as 40 dB to 45 dB, was derived. In FIG. 9, the horizontal axis represents time in units of ms, where the vertical axis represents potential in units of μV. As is clear from the scales shown in FIG. 9, the lower direction in the graph corresponds to plus (positive), and the upper direction corresponds to minus (negative). The baseline was set to an average potential from −200 ms to 0 ms.

In FIG. 9, the solid line shown represents the arithmetic mean waveform under the LF condition and LD condition defining a large sound pressure, whereas the broken line represents the arithmetic mean waveform under the SF condition and SD condition defining a small sound pressure. FIG. 9 indicates that the amplitude of the negative component in the negative direction, at a latency of about 200 ms, is larger in the solid line representing a large sound pressure than in the broken line representing a small sound pressure.

The negative peak value in the zone from 100 ms to 300 ms of each participant was −2.19 μV under the conditions defining a large sound pressure (LF/LD), and −1.41 μV under the conditions defining a small sound pressure (SF/SD). As a result of t-testing the waveform at each sampling point, significant differences existed in the zone from 218 ms to 238 ms and in the zone from 272 ms to 332 ms (p<0.05).

These results have led the inventors to the following conclusion concerning an event-related potential based on a point of audio presentation as a starting point: (1) a positive potential having a peak at a latency of about 700 ms reflects confidence of aural distinction, and this potential is available as an index of confidence of aural distinction; and (2) the potential at a latency of about 200 ms indicates a sound pressure level, and this potential is available for the determination as to whether the sound pressure of the stimulation audio was sufficient or not, apart from the determination as to confidence of aural distinction.

Concerning negative components, there have been reports that, when a pure tone is presented as a stimulation, an N1 component (a negative component at a latency around 100 ms) increases in amplitude with an increase in the sound pressure of the stimulation sound (for example, Naatanen, R., & Picton, T. W. (1987), The N1 wave of the human electric and magnetic response to sound: a review and an analysis of the component structure, Psychophysiology, 24, 375-425).

However, the amplitude of the N1 component changes depending not only on the sound pressure, but also on the rise and duration of the stimulation sound. Therefore, the relationship between the sound pressure level and negative components has not been clear in the case where a "speech sound", which undergoes changes in its rise, frequency, and power over time, is used as a stimulation.

When the sound pressure level is increased, the speech sound intelligibility usually improves. Therefore, it has not been clear as to whether a positive component at a latency of about 700 ms (which indicates confidence of aural distinction) and a negative component at a latency of about 200 ms are independent components from each other, and whether they are available for determination of the respective states.

Therefore, the fact that the negative component at a latency of about 200 ms increases in amplitude with an increase in the sound pressure of an audio stimulation, and the fact that the negative component at a latency of about 200 ms is independent from the confidence-reflecting positive component at a latency of about 700 ms, are believed to be unprecedented findings which had never been clear before the experiment by the inventors using four kinds of audio stimulations which were adapted in terms of ease of aural distinction and sound pressure.

The aforementioned positive component at a latency of about 700 ms (FIG. 8) and the negative component at a latency of about 200 ms for each sound pressure level (FIG. 9) at the electrode position Pz are distinguishable by a method of applying threshold processing to the loudnesses (amplitude) of peak values in the relevant zone, a method of generating templates from typical waveforms of these components and calculating similarity levels with such templates, and so on. Note that the threshold values and templates may be those of a typical user as previously stored, or may be generated for each individual person.

In this experiment, arithmetic means were taken from the data of eleven participants in order to confirm the fact that components which reflect the confidence of aural distinction and the sound pressure level appear in an event-related potential based on a point of audio presentation as a starting point. However, depending on the method of characteristic amount extraction (e.g., wavelet transformation of the waveform) or the method of identification (e.g., support vector machine learning), identification of a positive component is possible with no summations or only a small number of summations.

In the present specification, in order to define a component of an event-related potential, a point in time after the lapse of a predetermined time since a given point is expressed by referring to a "latency of about 700 ms", for example. This means possible inclusion of a range around the specific point of 700 ms in time. Generally speaking, there are 30 to 50 ms of differences (shifts) in event-related potential waveform between individuals, according to table 1 on p. 30 of "JISHOUKANRENDENI (ERP) MANYUARU-P300 WO CHUSHINNI- (or "Event-Related Potential (ERP) Manual-mainly concerning P300-"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 300 ms±30 ms, 700 ms±50 ms).

Although the aforementioned "breadth of 30 ms to 50 ms" is a generic example of an individual difference in the P300 component, greater individual differences exist between users with respect to the aforementioned positive component at a latency of about 700 ms, which is later in latency than P300. Therefore, the aforementioned positive component is preferably treated as having a broader breadth, e.g., a breadth of about 100 ms on each of the earlier side and the later side. Accordingly, in the present embodiment, a "latency of about 700 ms" is meant to indicate a latency of no less than 600 ms and no more than 800 ms.

Similarly, "near a latency of 200 ms" and "a latency of about 200 ms" may be construed as having a breadth of 30 ms to 50 ms on each of the earlier side and the later side of the latency of 200 ms, or even having a slightly greater breadth, e.g., a breadth of 50 ms to 100 ms on each of the earlier side and the later side. In other words, in the present embodiment, a "latency of about 200 ms" may be construed as a latency of no less than 100 ms and no more than 300 ms.

Thus, the inventors have found through their behavioral experiment that a speech sound intelligibility assessment can be made based on a user's confidence of aural distinction concerning audios. Moreover, through their electroencephalogram measurement experiment, they have found that (1) a positive component of an event-related potential at a latency of about 700 ms based on the point of audio presentation as a starting point reflects the confidence of aural distinction; and (2) independently from the positive component at a latency of about 700 ms indicating confidence of aural distinction, a negative component at a latency of about 200 ms based on the point of audio presentation as a starting point reflects the sound pressure level.

Therefore, with a method of estimating confidence of aural distinction concerning audios by using the positive component of an event-related potential as an index and estimating whether the sound pressure of a stimulation audio was sufficient by using the negative component of an event-related potential as an index, a detailed speech sound intelligibility assessment can be realized which requires no answer inputs.

FIG. 10A shows correspondence between presence or absence of a positive component and confidence of aural distinction and ease of hearing, as compiled by the inventors. First, paying attention to the presence or absence of the positive component, if the positive component is absent (i.e., the positive component does not appear), it is determined that the aural distinction was clear; if the positive component is present (i.e., the positive component appears), it is determined that the aural distinction was unclear. If unclearness of aural distinction is determined because of the presence of the positive component, it is then determined as to whether the sound pressure of the stimulation audio was sufficient or not based on the presence or absence of the negative component.

Note that a "positive component" would generally mean a potential which is greater than 0 μV. However, in the context of the present specification, it is not a requirement for a "positive component" to be absolutely positive (i.e., greater than 0 μV). In the present specification, the presence or absence of a "positive component" is identified in order to identify a high or low confidence of aural distinction; therefore, so long as a significant highness or lowness of confidence of aural distinction is distinguishable, it does not matter if the zone average potential, etc., is 0 μV or less.

FIG. 10B shows, in the case of unclear aural distinction, correspondence between presence or absence of a negative component and results of sound pressure level determination and estimated causes of unclearness. The determination of sufficiency of the sound pressure is made in such a manner that a sufficient sound pressure is determined when the negative component is present; and an insufficient sound pressure is determined when the negative component is absent.

Note that a "negative component" would generally mean a potential which is smaller than 0 μV. However, in the context of the present specification, it is not a requirement for a "negative component" to be absolutely negative (i.e., smaller than 0 μV). In the present specification, the presence or absence of a "negative component" is identified in order to identify a sufficient or insufficient sound pressure level; therefore, so long as an insufficient sound pressure is distinguishable, it does not matter if the zone average potential, etc., is 0 μV or more. Whenever the relative largeness and smallness of a negative component is distinguishable, it is described in terms of "presence or absence" of the negative component.

When the aural distinction is unclear in spite of a sufficient sound pressure, the cause of unclearness is likely to reside in consonants, which are smaller in power and pertain to different frequencies than vowels; thus, the cause can be estimated to be an insufficient gain of a consonant frequency of the presented speech sound, for example. On the other hand, in the case of an insufficient sound pressure, the cause of unclearness of aural distinction can be estimated to be an insufficient overall gain. Thus, diversification into specific fitting procedures can be achieved, e.g., increasing the gain of the consonant frequency if the cause of unclearness is an insufficient gain of the consonant frequency, or increasing the overall gain in the case of an insufficient overall gain.

Hereinafter, a speech sound intelligibility assessment system according to an embodiment of the present invention will be described. The speech sound intelligibility assessment system sequentially presents monosyllabic speech sounds in the form of audios, and makes an assessment of aural distinction concerning speech sounds based on a positive component of an event-related potential at a latency of about 700 ms based on a point of audio presentation as a starting point and on the presence or absence of a negative component at a latency of about 200 ms. Such a speech sound intelligibility assessment system, which does not require answer inputs by a user, is unprecedentedly realized by the aforementioned two findings by the inventors.

3. Embodiment 1

Hereinafter, the speech sound intelligibility assessment system will be first described in outline. Thereafter, the construction and operation of a speech sound intelligibility assessment system including a speech sound intelligibility assessment apparatus will be described.

The speech sound intelligibility assessment system of the present embodiment sequentially presents audios, and an event-related potential is measured based on each point of audio presentation as a starting point. Then, a positive component at a latency of about 700 ms, which appears when the confidence of aural distinction concerning audios is low, and a negative component at a latency around 200 ms, which increases in negative amplitude with the sound pressure of the stimulation audio, are detected; thus, the aural distinction concerning speech sounds is evaluated. The aforementioned positive component of the event-related potential reflects the confidence of aural distinction, and the negative component reflects the sound pressure level.

In the present embodiment, a probe electrode was placed at the parietal Pz, and a reference electrode was placed at the right or left mastoid, and an electroencephalogram was measured as a potential difference between the probe electrode and the reference electrode. Note that the levels and polarities of the characteristic components of the event-related potential may vary depending on the position at which the electrode for electroencephalogram measurement is attached, and the manner in which the reference electrode and the probe electrode are set. However, based on the following description, those skilled in the art would be able to detect a characteristic component of the event-related potential and make a speech sound intelligibility assessment by making appropriate modifications depending on the specific reference electrode and probe electrode being set. Any such variant is encompassed within the present invention.

Note that, in the above description of the electroencephalogram measurement experiment, the relative strength of the frequency gain is experimentally varied for participants with normal hearing, thus simulating the hearing of a person suffering from hypacusia. However, when making a speech sound intelligibility assessment for a person suffering from hypacusia, there is no particular need to present speech sounds that are difficult to aurally distinguish. In the present embodiment, it is assumed that speech sounds are presented whose gain for each frequency has been optimally adjusted based on a fitting method from audiograms of people suffering from hypacusia that were measured in advance.

Figure 11:
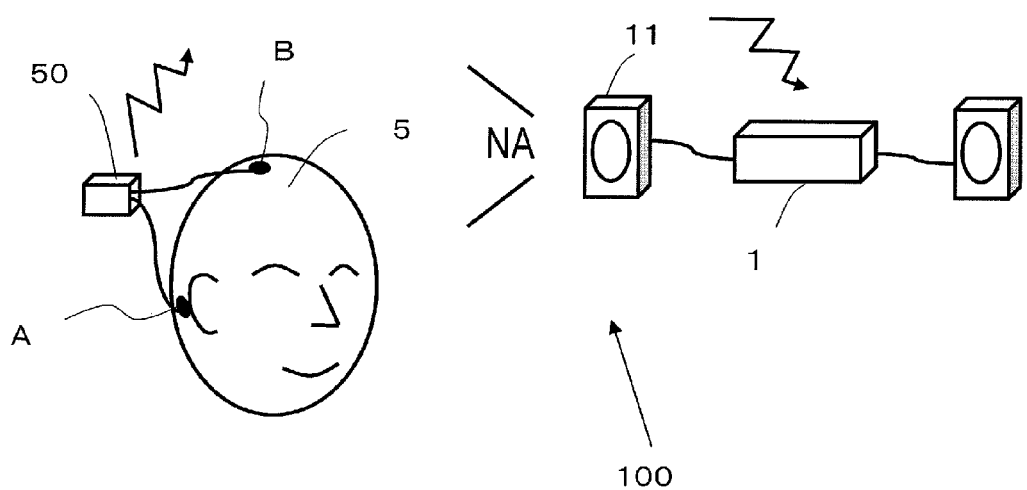
FIG. 11 is a diagram showing a construction and an environment of use for a speech sound intelligibility assessment system 100 according to Embodiment 1.

FIG. 11 shows a construction and an environment of use for a speech sound intelligibility assessment system 100 according to the present embodiment. The speech sound intelligibility assessment system 100 is exemplified so as to correspond to a system construction of Embodiment 1 described later.

The speech sound intelligibility assessment system 100 includes a speech sound intelligibility assessment apparatus 1, an audio output section 11, and a biological signal measurement section 50. The biological signal measurement section 50 is connected to at least two electrodes A and B. Electrode A is attached at a mastoid of the user 5, whereas electrode B is attached at a position (so-called Pz) on the scalp of the user 5.

The speech sound intelligibility assessment system 100 presents a monosyllabic speech sound to the user 5 in the form of an audio at a certain sound pressure, and determines the presence or absence of a positive component at a latency of about 700 ms in an electroencephalogram (event-related potential) from the user 5 which is measured based on the point of audio presentation as a starting point and the presence or absence of a negative component at a latency of about 200 ms. Then, based on the presented audio and the presence or absence of the positive component and the negative component, the speech sound intelligibility assessment system 100 automatically realizes a speech sound intelligibility assessment without answer inputs being made by the user 5.

An electroencephalogram from the user 5 is acquired by the biological signal measurement section 50 based on a potential difference between electrode A and electrode B. The biological signal measurement section 50 sends information corresponding to the potential difference to the speech sound intelligibility assessment apparatus 1 in a wireless or wired manner. FIG. 11 illustrates an example where the biological signal measurement section 50 wirelessly sends this information to the speech sound intelligibility assessment apparatus 1.

The speech sound intelligibility assessment apparatus 1 performs sound pressure control of the audio used for speech sound intelligibility assessment, controls presentation timing of the audio and the character, presents an audio via the audio output section 11 (e.g., loudspeakers) to the user 5.

Figure 12:
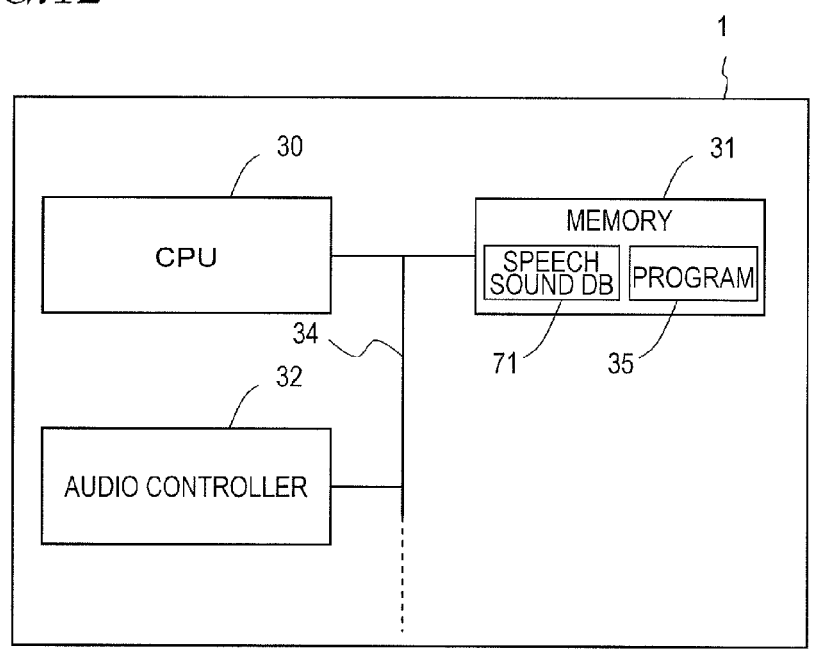
FIG. 12 is a diagram showing the hardware construction of a speech sound intelligibility assessment apparatus 1 according to Embodiment 1.

FIG. 12 shows a hardware construction of the speech sound intelligibility assessment apparatus 1 according to the present embodiment. The speech sound intelligibility assessment apparatus 1 includes a CPU 30, a memory 31, and an audio controller 32. These elements are interconnected via a bus 34 so that data exchange among them is possible.

The CPU 30, which is a computer composed of a semiconductor device, executes a computer program 35 which is stored in the memory 31. A processing procedure as illustrated by a subsequently-described flowchart is described in the computer program 35. In accordance with the computer program 35, the speech sound intelligibility assessment apparatus 1 performs a process of controlling the entire speech sound intelligibility assessment system 100, by utilizing a speech sound DB 71 which is also stored in the same memory 31. This process will be described in detail later.

In accordance with instructions from the CPU 30, the audio controller 32 generates an audio and a text character to be presented, and outputs the generated audio signal to the audio output section 11 at a designated sound pressure.

Note that the speech sound intelligibility assessment apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 12 (e.g., a PC) is able to function as the speech sound intelligibility assessment apparatus 1 according to the present embodiment. Note that the speech sound DB 71 does not need to be stored in the memory 31, but may be stored on a hard disk (not shown) which is connected to the bus 34.

Figure 13:
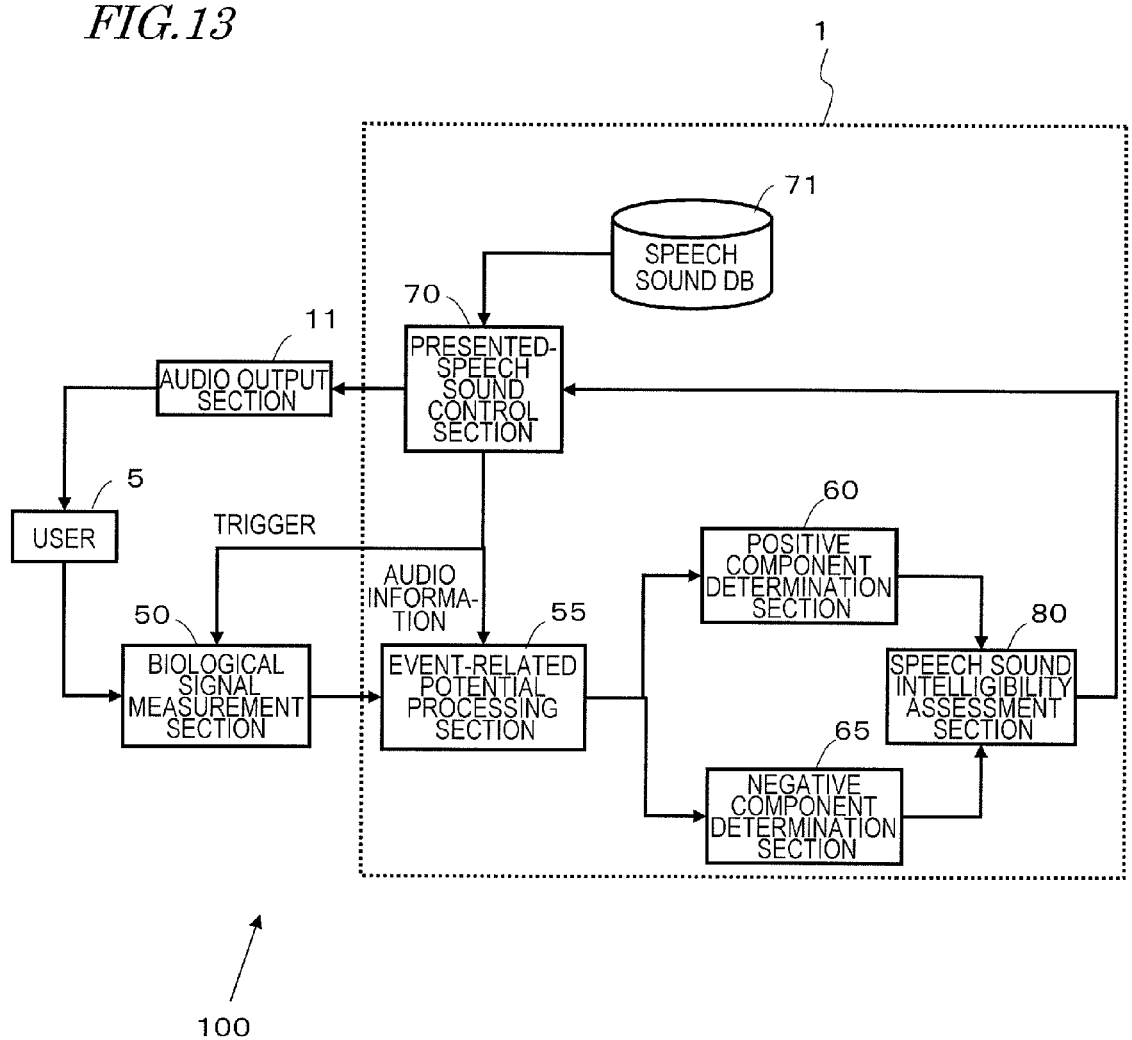
FIG. 13 is a diagram showing a functional block construction of the speech sound intelligibility assessment system 100 according to Embodiment 1.

FIG. 13 shows a functional block construction of the speech sound intelligibility assessment system 100 according to the present embodiment. The speech sound intelligibility assessment system 100 includes the audio output section 11, the biological signal measurement section 50, and the speech sound intelligibility assessment apparatus 1. FIG. 13 also shows detailed functional blocks of the speech sound intelligibility assessment apparatus 1. Specifically, the speech sound intelligibility assessment apparatus 1 includes an event-related potential processing section 55, a positive component determination section 60, a negative component determination section 65, a presented-speech sound control section 70, the speech sound DB 71, and a speech sound intelligibility assessment section 80. The user 5 block is illustrated for ease of explanation.

The respective functional blocks (except the speech sound DB 71) of the speech sound intelligibility assessment apparatus 1 correspond to functions which are realized by the CPU 30, the memory 31, and the audio controller 32 as a whole upon executing the program which has been described in conjunction with FIG. 12.

The speech sound DB 71 is a database of speech sounds which is provided for performing a speech sound intelligibility assessment. FIG. 14 shows an exemplary speech sound DB 71. In the speech sound DB 71 shown in FIG. 14, audio files to be presented, consonant labels, and grouped data based on likelihood of confusion (how likely confusion will occur) are associated. As for the stored audios, it is assumed that the gain adjustment for each frequency has been completed based on a fitting method from audiograms of people suffering from hypacusia that were measured in advance. The types of speech sounds to be stored may be speech sounds that are in the 57S list or the 67S list. The consonant labels are utilized when estimating a consonant that incurs a high probability of confusion by the user 5. The grouped data is utilized when estimating the group that incurs a high probability of confusion by the user 5. The grouping may be a rough category, a medium category, and a fine category, for example.

The rough category concerns categorization as to vowels, unvoiced consonants, and voiced consonants, which are respectively represented as 0, 1, and 2. The medium category defines sub-categorization among unvoiced consonants and among voiced consonants. The unvoiced consonants can be categorized into the sa-row (medium category: 1) and the ta-/ka-/ha-rows (medium category: 2), whereas the voiced consonants can be categorized into the ra-/ya-/wa-rows (medium category: 1) and the na/-ma-/ga-/za-/da-/ba-rows (medium category: 2). The fine category can be divided into the na-/ma-rows (fine category: 1) and the za-/ga-/da-/ba-rows (fine category: 2), for example. As for likelihood of confusion, the inventors relied on "HOCHOKI FITTINGU NO KANGAEKATA (or "Concept of Hearing Aid Fitting") (Kazuoki KODERA, Shindan To Chiryosha, 1999, p. 172).

FIG. 13 is again referred to. The presented-speech sound control section 70 determines a speech sound to be presented by referring to the speech sound DB 71. The speech sound may be selected and determined by random order, or determine it by receiving information of speech sounds which are yet to be evaluated or to be evaluated again from the speech sound intelligibility assessment section 100, for example. Moreover, in order to obtain information as to which consonant or which speech sound group will incur a high probability of confusion, the presented-speech sound control section 70 may select an audio of a particular consonant or speech sound group.

The presented-speech sound control section 70 presents the audio thus determined to the user 5 via the audio output section 11. Moreover, in accordance with the point of audio presentation, it sends a trigger to the biological signal measurement section 50, and the actual audio to be presented to the positive component determination section 60 and the negative component determination section 65.

The audio output section 11 reproduces and presents to the user 5 the monosyllabic audio which is designated by the presented-speech sound control section 70.

The biological signal measurement section 50, which is an electroencephalograph for measuring a biological signal of the user 5, measures an electroencephalogram as the biological signal. Then, the biological signal measurement section 50 cuts out an event-related potential in a predetermined zone (e.g., a zone from −200 ms to 1000 ms) based on the trigger received from the presented-speech sound control section 70 as a starting point, and sends it to the event-related potential processing section 55. It is assumed that the user 5 has already put on the electroencephalograph. The electrode for electroencephalogram measurement is attached at the parietal Pz, for example.

In accordance with the actual audio to be presented that is received from the presented-speech sound control section 70, the event-related potential processing section 55 takes an arithmetic mean of the event-related potentials received from the biological signal measurement section 50. The event-related potential processing section 55 may only select the event-related potentials for the same speech sound, thus taking an arithmetic mean of the event-related potentials for each speech sound type, for example. Taking an arithmetic mean only of the event-related potentials for the same speech sound makes possible an assessment of aural distinction for each speech sound.

The event-related potential processing section 55 sends the electroencephalogram data which has been obtained by taking an arithmetic mean over a predetermined number of times for each speech sound to the positive component determination section 60 and to the negative component determination section 65. Depending on the destination of electroencephalogram data, different processes may be performed for the event-related potential. For example, the number of times over which to take an arithmetic mean may be varied depending on the destination, or one of two kinds of filtering processes with different cutoff frequencies may be selected depending on the destination when performing a filtering process for the event-related potential waveform. As is also clear from FIG. 8 and FIG. 9, the positive component and the negative component differ in frequency, such that the negative component is of a higher frequency than the positive component. Therefore, electroencephalogram data with a high signal/noise ratio can be obtained by applying different filtering processes depending on the destination.

The positive component determination section 60 and the negative component determination section 65 receive the electroencephalogram data from the event-related potential processing section 55 and perform different analyses as will be described later.

Note that an arithmetic mean may be taken of selected speech sounds having the same consonant, or taken of each of the rough category, the medium category, and the fine category in the grouping shown in FIG. 14. Taking an arithmetic mean of speech sounds having the same consonant enables an assessment as to whether the intelligibility in aural distinction is low or not for each consonant type. Taking an arithmetic mean for each group enables an assessment of aural distinction as to the group, e.g., "between voiced consonants and unvoiced consonants, intelligibility in aural distinction is lower for the unvoiced consonants". From a consonant-by-consonant or group-by-group arithmetic mean, a summed waveform is obtained with more than a few summations being made.

Based on the electroencephalogram data received from the event-related potential processing section 55, the positive component determination section 60 determines the presence or absence of a positive component at a latency of about 700 ms. As has been discussed with respect to the earlier-described electroencephalogram measurement experiment, a "latency of about 700 ms" means a zone from 600 ms to 800 ms from a starting point, for example, the starting point being the point in time at which the audio output section 11 presents a speech sound.

The positive component determination section 60 identifies the presence or absence of the positive component by the following method. For example, the positive component determination section 60 compares the maximum amplitude at a latency of 700 ms or a zone average potential at a latency of 700 ms against a predetermined threshold value. Then, if the zone average potential is greater than the threshold value, the positive component determination section 60 may identify the case as "the positive component is present", or if the zone average potential is smaller than the threshold value, the positive component determination section 60 may identify the case as "the positive component is absent". Alternatively, by relying on a similarity level (e.g., a correlation coefficient) with a predetermined template which is generated from the waveform of a typical positive component signal at a latency of about 700 ms, if the similarity level is high, the positive component determination section 60 may identify the case as "the positive component is present", or if the similarity level is low, the positive component determination section 60 may identify the case as "the positive component is absent". The predetermined threshold value or template may be calculated or generated from a prestored waveform of a positive component of a generic user, or calculated or generated from the waveform of a positive component of each individual person.

The negative component determination section 65 identifies the presence or absence of a negative component at a latency of about 200 ms in the electroencephalogram data received from the event-related potential processing section 55. As has been discussed with respect to the earlier-described electroencephalogram measurement experiment, a "latency of about 200 ms" means a zone from 100 ms to 300 ms from a starting point, for example, the starting point being the point in time at which the audio output section 11 presents a speech sound.

The negative component determination section 65 identifies the presence or absence of the negative component by the following method. For example, the negative component determination section 65 compares the absolute value (amplitude) of a negative peak value at a latency of 200 ms against a predetermined threshold value. Then, if the absolute value (amplitude) of the negative peak value is equal to or greater than the threshold value, the negative component determination section 65 may identify the case as "the negative component is present", and if the absolute value of the peak value is smaller than the threshold value, the negative component determination section 65 may identify the case as "the negative component is absent". Alternatively, by relying on a similarity level (e.g., a correlation coefficient) with a predetermined template which is generated from the waveform of a typical negative component signal at a latency of about 200 ms, if the similarity level is high, the negative component determination section 60 may identify the case as "the negative component is present", or if the similarity level is low, the negative component determination section 60 may identify the case as "the negative component is absent". The predetermined threshold value or template may be calculated or generated from a prestored waveform of a negative component of a generic user, or calculated or generated from the waveform of a negative component of each individual person.

The speech sound intelligibility assessment section receives speech-sound-by-speech-sound information of the presence or absence of the positive component from the positive component determination section 60, and receives speech-sound-by-speech-sound information of the presence or absence of the negative component from the negative component determination section 65. Based on the received information, the speech sound intelligibility assessment section 100 makes a speech sound intelligibility assessment.

For example, the intelligibility assessment is made based on rules shown in FIGS. 10A and 10B and on the presence or absence of the positive component and the presence or absence of the negative component. As shown in FIG. 10A, first, the case where the electroencephalogram data lacks the positive component and indicates a high confidence of aural distinction is defined as "○" (=high intelligibility), whereas the case where the electroencephalogram data exhibits the positive component and indicates a low confidence of aural distinction is defined as "Δ" (=low intelligibility). A "high intelligibility" means that the user has clearly aurally comprehended the speech sound, whereas a "low intelligibility" means that the user has not clearly aurally comprehended the speech sound.

Now, it is assumed that the speech sound intelligibility assessment section 80 has made an assessment that the positive component is present and the intelligibility is low.

Then, the speech sound intelligibility assessment section 80 determines the presence or absence of the negative component in the electroencephalogram data. Based on the result of determination as to the presence or absence of the negative component and the criterion shown in FIG. 10B, the speech sound intelligibility assessment section 80 determines that the sound pressure level of the stimulation audio is sufficient if the negative component is present, or determines that the sound pressure level of the stimulation audio is insufficient if the negative component is absent.

FIGS. 15A and 15B show exemplary results of speech sound intelligibility assessment obtained by using the technique according to the present embodiment. FIGS. 15A and 15B show examples of evaluating the intelligibility of each speech sound based on a speech-sound-by-speech-sound arithmetic mean, respectively for user A and user B. First, based on the presence or absence of a positive component at a latency of about 700 ms in the electroencephalogram data, an intelligibility assessment is made so as to give ○ for the "positive component is absent" case and give Δ for the "positive component is present" case. Furthermore, in the case where the positive component is present but the aural distinction is unclear, the cause of unclearness is determined based on the presence or absence of a negative component at a latency of about 200 ms in the electroencephalogram data. The determination of the cause of unclearness is made on the basis that the sound pressure must be sufficient if the negative component is present and that the sound pressure must be insufficient if the negative component is absent. It can be understood from FIGS. 15A and 15B that, although the speech sound intelligibility is the same for both users, there are different causes of unclearness, that is: an insufficient overall gain for user A and insufficient gains of the consonant frequencies for user B. A proposal of a specific fitting procedure can be made for the example shown in FIGS. 15A and 15B: increase the overall gain for user A, and increase only the gains of the consonant frequencies of "な (na), ま (ma), ら (ra), だ (da)" for user B.

Figure 16:
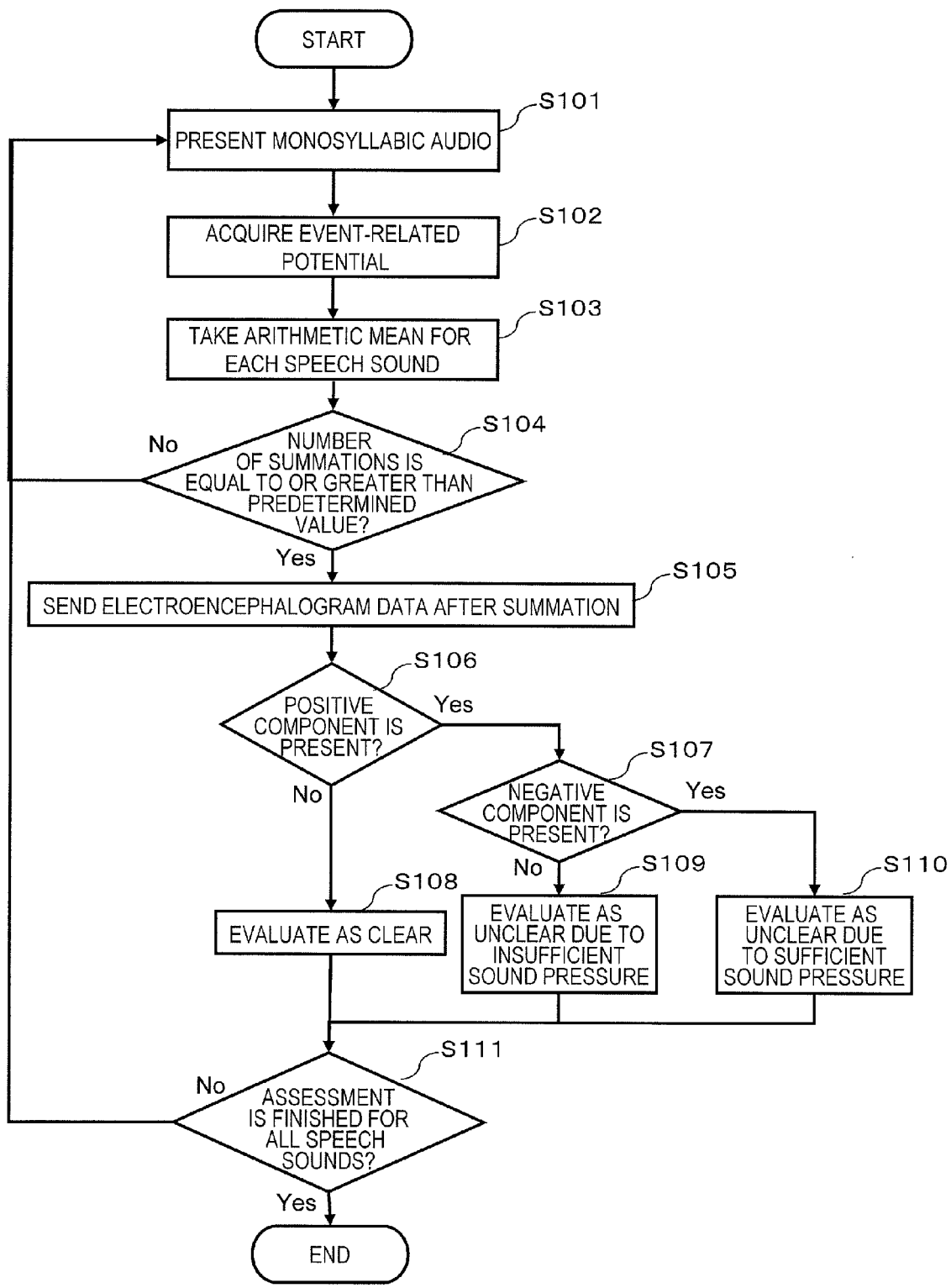
FIG. 16 is a flowchart showing a procedure of processing performed by the speech sound intelligibility assessment system 100.

Next, with reference to FIG. 16, an overall processing performed by the speech sound intelligibility assessment system 100 of FIG. 13 will be described. FIG. 16 is a flowchart showing a procedure of processing performed by the speech sound intelligibility assessment system 100.

At step S101, by referring to the speech sound DB 71, the presented-speech sound control section 70 determines a monosyllabic speech sound to be presented, presents the audio to the user 5 via the audio output section 11, and sends the information of the presented audio and a trigger to the positive component detection section 60. The speech sound to be presented may randomly be selected from the speech sound DB 71, or a speech sound of a particular consonant or a group may be exclusively selected.

At step S102, upon receiving the trigger from the presented-speech sound control section 70, the biological signal measurement section 50 cuts out an event-related potential from e.g. −200 ms to 1000 ms from the measured electroencephalogram, based on the trigger as a starting point. Then, an average potential from −200 ms to 0 ms is determined, and the resultant event-related potential is subjected to baseline correction so that this average potential becomes 0 μV.

At step S103, based on the information of the presented speech sound which is received from the presented-speech sound control section 70, the event-related potential processing section 55 takes an arithmetic mean of the event-related potential cut out at step S102 for each speech sound. Although it is assumed herein that the arithmetic mean is taken in a speech-sound-by-speech-sound manner, it may also be taken in a consonant-by-consonant or group-by-group manner.

At step S104, the event-related potential processing section 55 determines whether the number of summations for the event-related potential with respect to the speech sound presented at step S101 has reached a predetermined number of summations or not. If the number of summations is less than the predetermined number of times, the process returns to step S101 to repeat audio presentation. If the number of summations is equal to or greater than the predetermined number of times, the process proceeds to step S105.

At step S105, the event-related potential processing section 55 sends the electroencephalogram data obtained by taking an arithmetic mean over a predetermined number of times to the positive component determination section 60 and the negative component determination section 65.

At step S106, the positive component determination section 60 determines whether a positive component is present at a latency of about 700 ms in the electroencephalogram data. If it is not determined that the positive component is present, the process proceeds to step S108; if it is determined that the positive component is present, the process proceeds to step S107. Identification of the positive component may be performed through comparison against a threshold value or comparison against a template, as mentioned above.

At step S107, the negative component determination section 65 determines whether a negative component is present at a latency of about 200 ms in the electroencephalogram data. If it is not determined that the negative component is present, the process proceeds to step S109; if it is determined that the negative component is present, the process proceeds to step S110. Identification of the negative component may be performed through comparison against a threshold value or comparison against a template, as mentioned above.

At step S108, upon being informed by the positive component determination section 60 that no positive component is present at a latency of about 700 ms, the speech sound intelligibility assessment section 100 evaluates the speech sound presented at step S101 to be clear, and stores the result of assessment.

At step S109, upon being informed by the positive component determination section 60 that a positive component is present at a latency of about 700 ms and by the negative component determination section 65 that no negative component is present at a latency of about 200 ms, the speech sound intelligibility assessment section 100 evaluates the speech sound presented at step S101 to be unclear due to an insufficient sound pressure, and stores the assessment result.

At step S110, upon being informed by the positive component determination section 60 that a positive component is present at a latency of about 700 ms and by the negative component determination section 65 that a negative component is present at a latency of about 200 ms, the speech sound intelligibility assessment section 100 evaluates the speech sound presented at step S101 to be unclear although the sound pressure is sufficient, and stores the assessment result.

At step S111, the speech sound intelligibility assessment section 100 determines whether the intelligibility assessment has been completed for all of the speech sounds to be subjected to intelligibility assessment. If it is not complete, the process returns to step S101; if it is complete, the speech sound intelligibility assessment is ended.

The speech sound intelligibility assessment criteria are primarily based on the positive component as shown in FIG. 10A, and in the case of unclear aural distinction, an assessment of the cause of unclearness based on the presence or absence of the negative component follows, as shown in FIG. 10B.

Through the above process, on the premise that a monosyllabic speech sound is presented in the form of an audio, it is possible to make a speech sound intelligibility assessment at a given sound pressure level by using a positive component of an event-related potential at a latency of about 700 ms and a negative component at a latency of about 200 ms based on the point of audio presentation as a starting point, without answer inputs being made by a user. Moreover, the cause of unclearness can be distinguished to be either an insufficient sound pressure across all frequencies or an insufficient gain of the consonant frequency, which makes it easy to apply the assessment result to a specific fitting procedure.

Note that, since the speech sound intelligibility assessment apparatus 1 of the present embodiment is portable, a speech sound intelligibility assessment can be realized in any acoustic environment in which the user will be using a hearing aid.

The present embodiment has been illustrated by assuming a speech sound intelligibility assessment for the Japanese language. However, it may be English or Chinese so long as the speech sounds are monosyllabic. In the case of English, for example, monosyllabic words may be presented, and an evaluation may be made on a word-by-word basis. FIG. 17 shows exemplary assessment results for different monosyllabic words.

In accordance with the speech sound intelligibility assessment system 100 of the present embodiment, a speech sound intelligibility assessment is realized as the user merely hears an audio and thinks of a corresponding hiragana, without answer inputs being made. As a result, the trouble of a hearing aid user in making a speech sound intelligibility assessment at a hearing aid shop is reduced, for example. Moreover, the cause of unclearness can be distinguished to be either an insufficient sound pressure across all frequencies or an insufficient gain of the consonant frequency. This makes it easy to apply the speech sound intelligibility assessment result to a specific fitting procedure, thus realizing a fitting which allows conversations to be aurally distinguishable.

Although FIG. 11 illustrates the audio output section 11 as loudspeakers, the audio output section 11 may be headphones. Use of headphones, an enhanced mobility is provided, thus enabling a speech sound intelligibility assessment in an actual environment of use of the user.

4. Embodiment 2

In the speech sound intelligibility assessment system 100 of Embodiment 1, with respect to audios which have previously been adjusted according to one type of fitting method and stored in the speech sound DB 71, intelligibility is evaluated at a predetermined sound pressure level based on the presence or absence of a positive component at a latency of about 700 ms, and in the case of unclearness, the cause of unclearness is evaluated based on the presence or absence of a negative component at a latency of about 200 ms. The speech sound intelligibility assessment system 100 is characterized by its ability to identify the cause of unclearness to be an insufficient overall gain or an insufficient gain of the consonant frequency, thus realizing a switching of the specific fitting procedure to either increasing the overall sound volume or emphasizing the consonant frequency, for example.

However, from the assessment result at one sound pressure level alone, it is difficult to determine an optimum amount of adjustment for the overall sound volume or the gain for the consonant frequency, for example, this being inadequate for achieving an optimum fitting.

Accordingly, in a speech sound intelligibility assessment system described in the present embodiment, a loop is provided such that the audios in the speech sound DB are adjusted based on the cause of unclearness, and the speech sounds after adjustment are again subjected to a speech sound intelligibility assessment, thus to optimize the fitting parameters.

Figure 18:
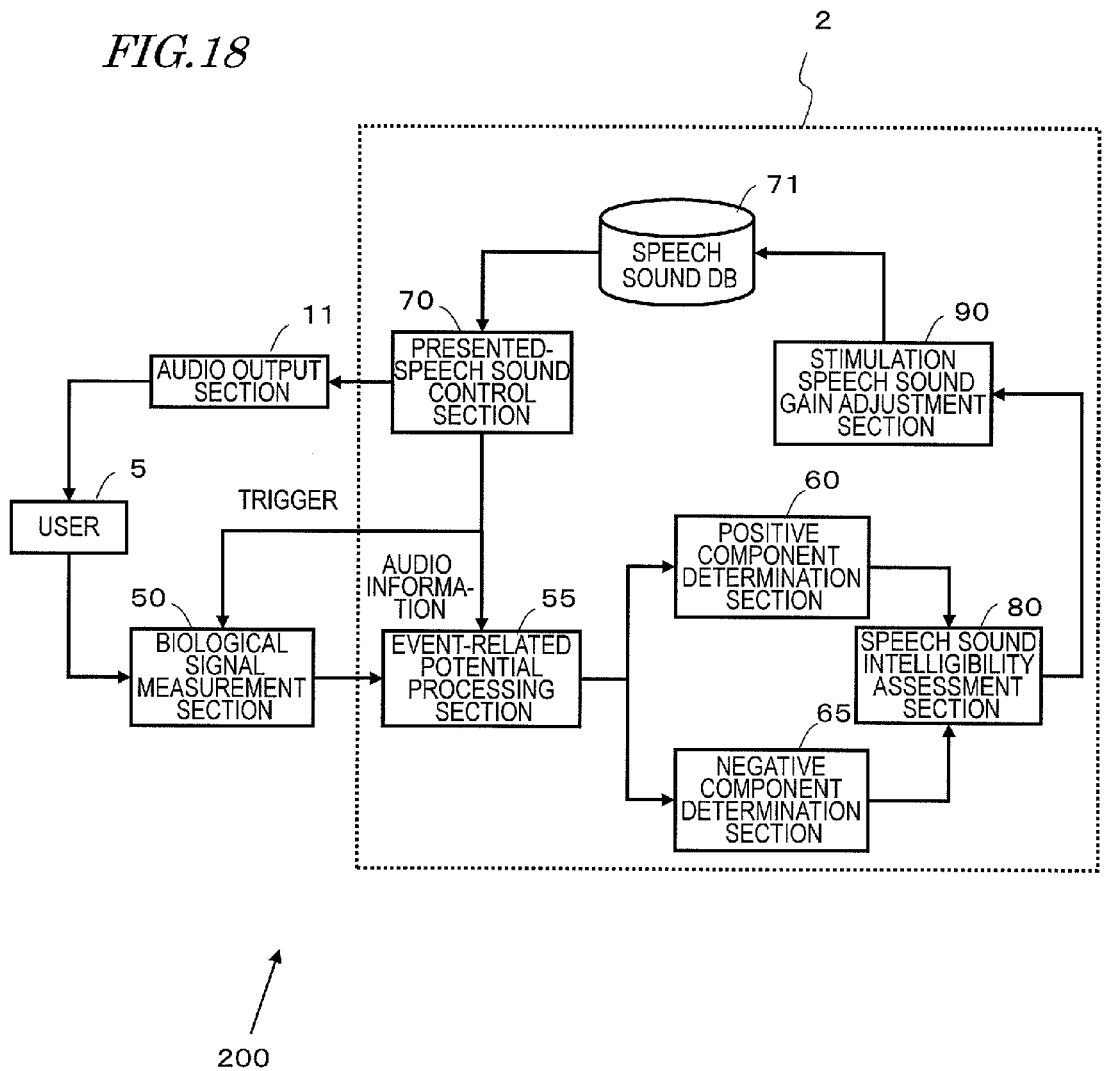
FIG. 18 is a diagram showing a functional block construction of a speech sound intelligibility assessment system 200 according to Embodiment 2.

FIG. 18 shows a functional block construction of a speech sound intelligibility assessment system 200 according to the present embodiment. The speech sound intelligibility assessment system 200 includes the audio output section 11, the biological signal measurement section 50, and a speech sound intelligibility assessment apparatus 2. Any block which has an identical counterpart in FIG. 13 is denoted by a like reference numeral, and the description thereof is omitted. The hardware construction of the speech sound intelligibility assessment apparatus 2 is as shown in FIG. 12. The speech sound intelligibility assessment apparatus 2 of the present embodiment shown in FIG. 18 is realized as a program which defines a different process from that of the program 35 described in Embodiment 1 (FIG. 12) is executed.

The speech sound intelligibility assessment apparatus 2 of the present embodiment differs from the speech sound intelligibility assessment apparatus 1 of Embodiment 1 in that a stimulation speech sound gain adjustment section 90 is additionally introduced.

Hereinafter, the stimulation speech sound gain adjustment section 90 will be described.

The stimulation speech sound gain adjustment section 90 receives intelligibilities (e.g., speech-sound-by-speech-sound intelligibilities) stored in the speech sound intelligibility assessment section 80 and the assessment results concerning the causes of unclearness as shown in FIGS. 15A and 15B. Then, in the case of unclearness, the stimulation speech sound gain adjustment section 90 determines an amount of gain adjustment for the stimulation speech sound for each cause of unclearness, and updates the speech sound data in the speech sound DB 71.

For example, if the cause of unclearness is "insufficient overall gain", the gain of all frequency ranges is increased by 5 dB. If the cause of unclearness is "insufficient gain of the consonant frequency", the consonant frequency band of the speech sound of interest is calculated, and the gain of this frequency band is increased by 5 dB. In the case where the speech sound intelligibility assessment section 80 has performed an intelligibility assessment in a consonant-label-by-consonant-label or group-by-group manner according to FIG. 14, a consonant frequency band may be calculated in a consonant-label-by-consonant-label or group-by-group manner.

The amount of gain adjustment is not limited to 5 dB, but may be 3 dB or 7 dB. Moreover, the amount of gain adjustment may be reduced according to the number of updates having been made to the speech sound data.

In the case where the initial audio data stored in the speech sound DB 71 is audio data whose frequency-gain characteristics has been adjusted based on an audiogram and a fitting theory of each individual user, the frequency-gain characteristics of that adjustment method may be stored as the initial frequency-gain characteristics in the stimulation speech sound gain adjustment section 90.

Figure 19:
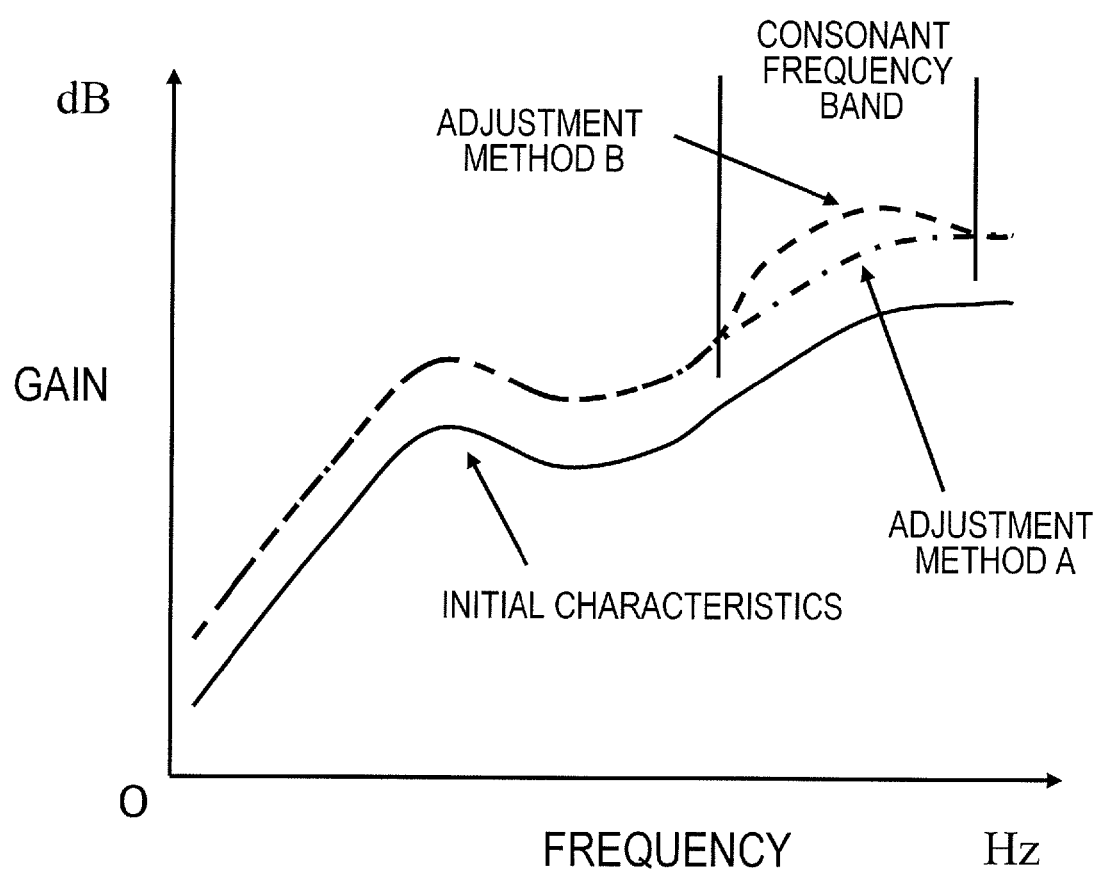
FIG. 19 is a diagram showing: initial characteristics of frequency-gain characteristics stored in a stimulation speech sound gain adjustment section 90; frequency-gain characteristics under adjustment method A, which increases the overall gain from the initial characteristics; and frequency-gain characteristics under adjustment method B, which increases the gain in a consonant frequency band of a target speech sound from adjustment method A.

With reference to FIG. 19 and FIGS. 20A to 20C, an exemplary stimulation speech sound gain adjustment method in the stimulation speech sound gain adjustment section 90 will be described. First, the solid line (initial characteristics) in FIG. 19 represents, as the initial frequency-gain characteristics stored in the stimulation speech sound gain adjustment section 90, frequency-gain characteristics which have been determined from an audiogram and a fitting theory. A user having poor hearing of higher sounds is contemplated, and thus an adjustment pattern for emphasizing the gain for higher sounds is illustrated.

FIG. 20A shows speech sound intelligibility assessment results for a user when hearing audio stimulations which have been subjected to a gain adjustment according to these initial characteristics. As shown in FIG. 20A, it is assumed that the cause of unclearness for any and every speech sound whose aural distinction was unclear was "insufficient overall gain". In this case, the stimulation speech sound gain adjustment section 90 selects "increase the overall gain" as the adjustment method. Then, the stimulation speech sound gain adjustment section 90 generates speech sound stimulations whose gain is increased by 5 dB across all frequencies, and updates the speech sound data in the speech sound DB 71. The dot-dash line in FIG. 19 illustrates frequency-gain characteristics whose overall gain is increased from the initial characteristics according to adjustment method A.

FIG. 20B shows exemplary results of speech sound intelligibility assessment made in the speech sound intelligibility assessment section 80 for a user when hearing audio stimulations which have been adjusted by adjustment method A. FIG. 20B indicates that adjustment method A has eliminated unclearness of aural distinction for the most part, and that the remaining cause of unclearness of aural distinction is an "insufficient gain of the consonant frequency".

Based on the results of intelligibility assessment shown in FIG. 20B, the stimulation speech sound gain adjustment section 90 first calculates a consonant frequency band of the speech sound of interest (which is "さ(sa)" in FIG. 21), and increases the gain of the calculated consonant frequency band by 5 dB, for example. The broken line (adjustment method B) in FIG. 19 represents frequency-gain characteristics obtained by increasing the gain of the consonant frequency band of the target speech sound from adjustment method A. The stimulation speech sound gain adjustment section 90 updates the speech sound data in the speech sound DB with the audio which has been adjusted according to the frequency-gain characteristics of adjustment method B.

FIG. 20C shows exemplary results of speech sound intelligibility assessment for the speech sounds which have been adjusted by adjustment method B. FIG. 20C indicates that all speech sounds have now become clearly aurally distinguishable through the two adjustment methods.

Next, with reference to the flowchart of FIG. 21, an overall procedure of processing that is performed in the speech sound intelligibility assessment system 200 will be described.

FIG. 21 shows a processing procedure by the speech sound intelligibility system 200 of the present embodiment. In FIG. 21, any step where a process identical to a process by the speech sound intelligibility assessment system 100 (FIG. 16) will be denoted by a like reference numeral, and the description thereof will be omitted.

The processes by the speech sound intelligibility assessment system 200 of the present embodiment differ from the processes of the speech sound intelligibility assessment system 200 of Embodiment 1 in that the following steps are added: step S201, which involves branching based on whether there is any unclearness result among the speech sound intelligibility assessment results, and steps S202 to S205 of updating the speech sound data in the speech sound DB with the stimulation audios which have been adjusted with respect to the respective causes of unclearness. Any step other than these additional steps have already been described in connection with FIG. 16, and the descriptions thereof are omitted.

At step S201, the stimulation speech sound gain adjustment section 90 determines whether the speech sound intelligibility assessment results received from the speech sound intelligibility assessment section 80 include any unclearness results. If any unclearness results are included among the speech sound intelligibility assessment results, the process proceeds to step S202; if not, the process proceeds to END.

At step S202, the stimulation speech sound gain adjustment section 90 determines whether the cause of unclearness of the speech sound intelligibility assessment results received from the speech sound intelligibility assessment section 80 is an insufficient overall gain or not. If it is an insufficient overall gain, the process proceeds to step S203; if it is an insufficient gain of the consonant frequency, the process proceeds to step S204.

At step S203, the stimulation speech sound gain adjustment section 90 generates stimulation speech sounds whose overall gain is increased by e.g. 5 dB, and updates the audio data in the speech sound DB 71.

At step S204, the stimulation speech sound gain adjustment section 90 calculates a consonant frequency band of each speech sound which is unclear because of an insufficient gain of the consonant frequency.

At step S205, the stimulation speech sound gain adjustment section 90 generates a stimulation audio(s) whose gain(s) in the consonant frequency band(s) calculated at step S204 is/are increased by e.g. 5 dB, and updates the audio data in the speech sound DB 71.

Through such processes, the loop involving a speech sound intelligibility assessment, a frequency gain adjustment for each cause of unclearness, and a speech sound intelligibility assessment for the adjusted stimulation speech sounds makes it possible to automatically optimize the fitting parameters. Note that it will also be possible to reduce the intelligibility assessment time by allowing only the speech sounds whose audio data have been updated to be again subjected to an intelligibility assessment in the stimulation speech sound gain adjustment section 90.

Since the speech sound intelligibility assessment apparatus 2 of the present embodiment is portable, a speech sound intelligibility assessment can be realized in any acoustic environment in which the user will be using a hearing aid.

In accordance with the speech sound intelligibility assessment system 200 of the present embodiment, it is possible to easily and automatically ascertain optimum fitting parameters for each user. This eliminates the need for any fitting to be made for searching purposes, and thus significantly reduces the amount of time required for fitting.

In the above embodiments, the speech sound DB is illustrated as being incorporated within the speech sound intelligibility assessment apparatus. However, this is only an example. The speech sound DB may be provided external to the speech sound intelligibility assessment apparatus, and referred to by the speech sound intelligibility assessment apparatus in a wireless or wired manner. For example, the speech sound DB may be stored on a memory card, which may be inserted in the speech sound intelligibility assessment apparatus upon use of the speech sound intelligibility assessment system. Alternatively, the speech sound DB may be stored at a server on the Internet, and referred to by the speech sound intelligibility assessment apparatus via the Internet upon use of the speech sound intelligibility assessment system. In such cases, the speech sound DB is not an element of the speech sound intelligibility assessment apparatus. Similarly, the speech sound DB does not need to be an element of the speech sound intelligibility assessment system.

A speech sound intelligibility assessment apparatus according to the present invention and a speech sound intelligibility assessment system incorporating the speech sound intelligibility assessment apparatus can automatically make an assessment of speech sound intelligibility, and can be used for the fitting of a hearing aid by all kinds of people, including users who cannot answer with speech or button pressing, e.g., physically handicapped users and infants.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A speech sound intelligibility assessment system comprising:
   a speech sound database retaining a plurality of speech sounds;
   a presented-speech sound control section for determining a speech sound to be presented by referring to the speech sound database;
   an output section for presenting the determined speech sound to a user;
   a biological signal measurement section for measuring an electroencephalogram signal of the user;
   a positive component determination section for determining presence or absence of a positive component of an event-related potential in the electroencephalogram signal in a zone from 600 ms to 800 ms from a starting point, the starting point being a point in time at which the output section presents a speech sound;
   a negative component determination section for determining presence or absence of a negative component of an event-related potential in the electroencephalogram signal in a zone from 100 ms to 300 ms from a starting point, the starting point being a point in time at which the output section presents a speech sound; and
   a speech sound intelligibility assessment section for evaluating whether the user has clearly aurally comprehended the presented speech sound or not, based on a result of determination as to presence or absence of the positive component acquired from the positive component determination section and a result of determination as to presence or absence of the negative component acquired from the negative component determination section;

wherein the speech sound intelligibility assessment section:
      makes an evaluation that the user has clearly aurally comprehended the presented speech sound when the result of determination by the positive component determination section indicates that the positive component is absent;
      makes an evaluation that the user has not clearly aurally comprehended the presented speech sound due to an insufficient overall sound pressure when the result of determination by the positive component determination section indicates that the positive component is present and the result of determination by the negative component determination section indicates that the negative component is absent; or
      makes an evaluation that the user has not clearly aurally comprehended the presented speech sound due to an insufficient sound pressure of a consonant frequency when the result of determination by the positive component determination section indicates that the positive component is present and the result of determination by the negative component determination section indicates that the negative component is present.

2. The speech sound intelligibility assessment system of claim 1, wherein
   the positive component determination section compares between a predetermined threshold value and a zone average potential of an event-related potential in a zone from 600 ms to 800 ms from a starting point, the starting point being a point in time at which the output section presents a speech sound, and
   determines that the positive component is present when the zone average potential is equal to or greater than the threshold value, or
   determines that the positive component is absent when the zone average potential is smaller than the threshold value.

3. The speech sound intelligibility assessment system of claim 1, wherein
   the negative component determination section compares between a predetermined threshold value and an absolute value of a negative peak value of an event-related potential in a zone from 100 ms to 300 ms from a starting point, the starting point being a point in time at which the output section presents a speech sound, and
   determines that the negative component is present when the absolute value of the peak value is equal to or greater than the threshold value, or
   determines that the negative component is absent when the absolute value of the peak value is smaller than the threshold value.

4. The speech sound intelligibility assessment system of claim 1, wherein, in the speech sound database, a speech sound type, consonant information type, and a group concerning probability of confusion are associated with each of the plurality of speech sounds retained therein.

5. The speech sound intelligibility assessment system of claim 1, wherein
   the speech sound database further retains gain information defining a gain for each of frequency bands concerning the plurality of speech sounds, the speech sound intelligibility assessment system further comprising:
   a stimulation speech sound gain adjustment section for, with respect to any speech sound that is evaluated by the speech sound intelligibility assessment section as not being clearly aurally comprehended by the user due to an insufficient overall sound pressure, updating the frequency-by-frequency gain information concerning speech sounds that is retained in the speech sound database so as to increase the gain for the entire frequency band, and with respect to any speech sound that is evaluated by the speech sound intelligibility assessment section as not being clearly aurally comprehended by the user due to an insufficient sound pressure of a consonant frequency, calculating a consonant frequency band of the speech sound and updating the frequency-by-frequency gain information concerning speech sounds that is retained in the speech sound database so as to increase the gain for the consonant frequency band.

6. A speech sound intelligibility assessment comprising:
a speech sound database retaining a plurality of speech sounds;
a presented-speech sound control section for determining a speech sound to be presented by referring to the speech sound database;
an output section for presenting the determined speech sound to a user;
a biological signal measurement section for measuring an electroencephalogram signal of the user;
a positive component determination section for determining presence or absence of a positive component of an event-related potential in the electroencephalogram signal in a zone from 600 ms to 800 ms from a starting point, the starting point being a point in time at which the output section presents a speech sound;
a negative component determination section for determining presence or absence of a negative component of an event-related potential in the electroencephalogram signal in a zone from 100 ms to 300 ms from a starting point, the starting point being a point in time at which the output section presents a speech sound; and
a speech sound intelligibility assessment section for evaluating whether the user has clearly aurally comprehended the presented speech sound or not, based on a result of determination as to presence or absence of the positive component acquired from the positive component determination section and a result of determination as to presence or absence of the negative component acquired from the negative component determination section;
wherein, in the speech sound database, a speech sound type, consonant information type, and a group concerning probability of confusion are associated with each of the plurality of speech sounds retained therein; and
further comprising an event-related potential processing section for referring to association between the speech sound type, the consonant information type, and the group concerning probability of confusion stored in the speech sound database, and generating electroencephalogram data by taking an arithmetic mean of event-related potentials corresponding to the presented speech sound, with respect to each of the speech sound type, the consonant information type, and the group concerning probability of confusion.

7. The speech sound intelligibility assessment system of claim 6, wherein,
the output section presents a plurality of speech sounds;
the positive component determination section and the negative component determination section receive electroencephalogram data obtained by taking an arithmetic mean of event-related potentials with respect to each speech sound type, each consonant type, or each group concerning probability of confusion in connection with the presented plurality of speech sounds;
based on the electroencephalogram data, the positive component determination section determines presence or absence of the positive component of the event-related potential with respect to each speech sound type, each consonant type, or each group concerning probability of confusion; and
based on the electroencephalogram data, the negative component determination section determines presence or absence of the negative component of the event-related potential with respect to each speech sound type, each consonant type, or each group concerning probability of confusion.

8. A speech sound intelligibility assessment method comprising the steps of:
providing a speech sound database retaining a plurality of speech sounds;
determining a speech sound to be presented by referring to the speech sound database;
presenting the determined speech sound to a user;
measuring an electroencephalogram signal of the user;
determining presence or absence of a positive component of an event-related potential in the electroencephalogram signal in a zone from 600 ms to 800 ms from a starting point, the starting point being a point in time at which the output section presents a speech sound;
determining presence or absence of a negative component of an event-related potential in the electroencephalogram signal in a zone from 100 ms to 300 ms from a starting point, the starting point being a point in time at which the output section presents a speech sound; and
evaluating whether the user has clearly aurally comprehended the presented speech sound or not based on a result of determination of presence or absence of the positive component and a result of determination of presence or absence of the negative component;
wherein the evaluating step:
makes an evaluation that the user has clearly aurally comprehended the presented speech sound when a result of determination of presence or absence of the positive component indicates that the positive component is absent;
makes an evaluation that the user has not clearly aurally comprehended the presented speech sound due to an insufficient overall sound pressure when a result of determination of presence or absence of the positive component indicates that the positive component is present and a result of determination of presence or absence of the negative component indicates that the negative component is absent; or
makes an evaluation that the user has not clearly aurally comprehended the presented speech sound due to an insufficient sound pressure of a consonant frequency when a result of determination of presence or absence of the positive component indicates that the positive component is present and a result of determination of presence or absence of the negative component indicates that the negative component is present.

9. A computer program, stored on a non-transitory computer-readable medium, to be executed by a computer mounted in a speech sound intelligibility assessment system including a speech sound database retaining a plurality of speech sounds, wherein
the computer program causes the computer in the speech sound intelligibility assessment system to execute the steps of:
determining a speech sound to be presented by referring to the speech sound database;

presenting the determined speech sound to a user;
measuring an electroencephalogram signal of the user;
determining presence or absence of a positive component of an event-related potential in the electroencephalogram signal in a zone from 600 ms to 800 ms from a starting point, the starting point being a point in time at which the output section presents a speech sound;
determining presence or absence of a negative component of an event-related potential in the electroencephalogram signal in a zone from 100 ms to 300 ms from a starting point, the starting point being a point in time at which the output section presents a speech sound; and
evaluating a speech sound intelligibility indicating whether the user has clearly aurally comprehended the presented speech sound or not based on a result of determination of presence or absence of the positive component and a result of determination of presence or absence of the negative component;
wherein the evaluating step:
    makes an evaluation that the user has clearly aurally comprehended the presented speech sound when a result of determination of presence or absence of the positive component indicates that the positive component is absent;
    makes an evaluation that the user has not clearly aurally comprehended the presented speech sound due to an insufficient overall sound pressure when a result of determination of presence or absence of the positive component indicates that the positive component is present and a result of determination of presence or absence of the negative component indicates that the negative component is absent; or
    makes an evaluation that the user has not clearly aurally comprehended the presented speech sound due to an insufficient sound pressure of a consonant frequency when a result of determination of presence or absence of the positive component indicates that the positive component is present and a result of determination of presence or absence of the negative component indicates that the negative component is present.

10. A speech sound intelligibility assessment apparatus comprising:
    a presented-speech sound control section for determining a speech sound to be presented by referring to a speech sound database retaining a plurality of speech sounds;
    a positive component determination section for determining presence or absence of a positive component of an event-related potential in an electroencephalogram signal of a user measured by a biological signal measurement section in a zone from 600 ms to 800 ms from a starting point, the starting point being a point in time at which the speech sound is presented;
    a negative component determination section for determining presence or absence of a negative component in an event-related potential in the electroencephalogram signal in a zone from 100 ms to 300 ms from a starting point, the starting point being a point in time at which a speech sound is presented by an output section; and
    a speech sound intelligibility assessment section for evaluating whether the user has clearly aurally comprehended the presented speech sound or not based on a result of determination as to presence or absence of the positive component acquired from the positive component determination section and a result of determination as to presence or absence of the negative component acquired from the negative component determination section;
    wherein the speech sound intelligibility assessment section:
        makes an evaluation that the user has clearly aurally comprehended the presented speech sound when the result of determination by the positive component determination section indicates that the positive component is absent;
        makes an evaluation that the user has not clearly aurally comprehended the presented speech sound due to an insufficient overall sound pressure when the result of determination by the positive component determination section indicates that the positive component is present and the result of determination by the negative component determination section indicates that the negative component is absent; or
        makes an evaluation that the user has not clearly aurally comprehended the presented speech sound due to an insufficient sound pressure of a consonant frequency when the result of determination by the positive component determination section indicates that the positive component is present and the result of determination by the negative component determination section indicates that the negative component is present.

11. A method of operating a speech sound intelligibility assessment system, comprising:
    a step where a presented-speech sound control section determines a speech sound to be presented by referring to a speech sound database retaining a plurality of speech sounds;
    a step where an output section presents the determined speech sound to a user;
    a step where an electroencephalogram measurement section measures an electroencephalogram signal of the user;
    a step where a positive component determination section determines presence or absence of a positive component of an event-related potential in the electroencephalogram signal in a zone from 600 ms to 800 ms from a starting point, the starting point being a point in time at which the output section presents a speech sound;
    a step where a negative component determination section determines presence or absence of a negative component of an event-related potential in the electroencephalogram signal in a zone from 100 ms to 300 ms from a starting point, the starting point being a point in time at which the output section presents a speech sound; and
    a step where a speech sound intelligibility assessment section evaluates whether the user has clearly aurally comprehended the presented speech sound or not based on a result of determination of presence or absence of the positive component and a result of determination of presence or absence of the negative component;
    wherein the evaluating step by the speech sound intelligibility assessment section:
        makes an evaluation that the user has clearly aurally comprehended the presented speech sound when a result of determination of presence or absence of the positive component indicates that the positive component is absent;
        makes an evaluation that the user has not clearly aurally comprehended the presented speech sound due to an insufficient overall sound pressure when a result of determination of presence or absence of the positive component indicates that the positive component is present and a result of determination of presence or absence of the negative component indicates that the negative component is absent; or makes an evaluation that the user has not clearly aurally comprehended the presented speech sound due to an insufficient sound pressure of a consonant frequency when a result of determination of presence or absence of the positive component indicates that the positive component is present and a result of determination of presence or absence of the negative component indicates that the negative component is present.

12. A speech sound intelligibility assessment system comprising:

a speech sound database retaining a plurality of speech sounds;

a presented-speech sound control section for determining a speech sound to be presented by referring to the speech sound database;

an output section for presenting the determined speech sound to a user;

a biological signal measurement section for measuring an electroencephalogram signal of the user;

a positive component determination section for determining presence or absence of a positive component of an event-related potential in the electroencephalogram signal in a zone from 600 ms to 800 ms from a starting point, the starting point being a point in time at which the output section presents a speech sound;

a negative component determination section for determining presence or absence of a negative component of an event-related potential in the electroencephalogram signal in a zone from 100 ms to 300 ms from a starting point, the starting point being a point in time at which the output section presents a speech sound; and a speech sound intelligibility assessment section for evaluating whether the user has clearly aurally comprehended the presented speech sound or not, based on a result of determination as to presence or absence of the positive component acquired from the positive component determination section and a result of determination as to presence or absence of the negative component acquired from the negative component determination section; and a stimulation speech sound gain adjustment section for, when the positive component is absent and the negative component is absent, increasing the gain for the entire frequency band; or when the positive component is absent and the negative component is present, calculating a consonant frequency band of the speech sound and increasing the gain for the consonant frequency band;

wherein the speech sound intelligibility assessment section:

makes an evaluation that the user has clearly aurally comprehended the presented speech sound when the result of determination by the positive component determination section indicates that the positive component is absent;

makes an evaluation that the user has not clearly aurally comprehended the presented speech sound due to an insufficient overall sound pressure when the result of determination by the positive component determination section indicates that the positive component is present and the result of determination by the negative component determination section indicates that the negative component is absent; or makes an evaluation that the user has not clearly aurally comprehended the presented speech sound due to an insufficient sound pressure of a consonant frequency when the result of determination by the positive component determination section indicates that the positive component is present and the result of determination by the negative component determination section indicates that the negative component is present.

* * * * *